United States Patent
Wang

(10) Patent No.: US 9,480,664 B2
(45) Date of Patent: Nov. 1, 2016

(54) COMPOSITIONS AND METHODS FOR TREATING CANCER

(71) Applicant: Augusta University Research Institute, Inc., Augusta, GA (US)

(72) Inventor: Mong-Heng Wang, Martinez, GA (US)

(73) Assignee: Augusta University Research Institute, Inc., Augusta, GA (US)

( * ) Notice: Subject to any disclaimer, the term of this patent is extended or adjusted under 35 U.S.C. 154(b) by 0 days.

(21) Appl. No.: 14/809,859

(22) Filed: Jul. 27, 2015

(65) Prior Publication Data

US 2016/0022614 A1    Jan. 28, 2016

Related U.S. Application Data

(60) Provisional application No. 62/028,835, filed on Jul. 25, 2014.

(51) Int. Cl.
| | |
|---|---|
| *A61K 31/34* | (2006.01) |
| *A61K 31/155* | (2006.01) |
| *A61K 31/5575* | (2006.01) |
| *A61K 45/06* | (2006.01) |
| *A61K 31/365* | (2006.01) |

(52) U.S. Cl.
CPC ........... *A61K 31/155* (2013.01); *A61K 31/365* (2013.01); *A61K 31/5575* (2013.01); *A61K 45/06* (2013.01)

(58) Field of Classification Search
USPC ...................................................... 514/473
See application file for complete search history.

(56) References Cited

PUBLICATIONS

Miyata et al. CAS: 135: 235866, 2001.*
Zhang et al. publication, American Journal of Physiology, 2014, 307(3): R693-R703.*
Alexanian, et al., "Down-regulation of 20-HETE synthesis and signaling inhibits renal adenocarcinoma cell proliferation and tumor growth", Anticancer Res., 29:3819-24 (2009).
Arber, et al., "Five-year analysis of the prevention of colorectal sporadic adenomatous polyps trial", Am J Gastroenterol., 106:1135-46 (2011).
Bertagnolli , et al., "Celecoxib for the prevention of sporadic colorectal adenomas", N Engl J Med., 355: 873-84 (2006).
Bresalier, et al., "Cardiovascular events associated with rofecoxib in a colorectal adenoma chemoprevention trial" N Engl J Med., 352:1092-102 (2005).
Carroll, et al., "Cyclooxygenase dependency of the renovascular actions of cytochrome P450-derived arachidonate metabolites", J Pharmacol Exp Ther,, 260:104-9 (1992).
Chen, et al., "Beneficial effects of inhibition of soluble epoxide hydrolase on glucose homeostasis and islet damage in a streptozotocin-induced diabetic mouse model", Prostaglandins Other Lipid Mediat., 104-105:42-48 (2013).
Fitzgerald, "Coxibs and cardiovascular disease", N Engl J Med., 351:1709-11 (2004).
Funk, et al., "COX-2 inhibitors and cardiovascular risk", J Cardiovasc Pharmacol., 50: 470-9 (2007).
Gebremedhin, et al., "Cat cerebral arterial smooth muscle cells express cytochrome P450 4A2 enzyme and produce the vasoconstrictor 20-HETE which enhances L-type Ca2+ current", J Physiol., 507 ( Pt 3):771-81 (1998).
Guo, et al., "9L gliosarcoma cell proliferation and tumor growth in rats are suppressed by N-hydroxy-N'-(4-butyl-2-methylphenol) formamidine (HET0016), a selective inhibitor of CYP4A", J Pharmacol Exp Ther., 317: 97-108 (2006).
Guo, et al., "Expression of CYP4A1 in U251 human glioma cell induces hyperproliferative phenotype in vitro and rapidly growing tumors in vivo", J Pharmacol Exp Ther., 327:10-9 (2008).
Hoda, et al., "Sex-independent neuroprotection with minocycline after experimental thromboembolic stroke", Exp Transl Stroke Med., 3:16 (2011).
Konson, et al., "Herpes simplex virus thymidine kinase gene transduction enhances tumor growth rate and cyclooxygenase-2 expression in murine colon cancer cells" , Cancer Gene Ther., 11: 830-40 (2004).
Konson, et al., "The involvement of nuclear factor-kappa B in cyclooxygenase-2 overexpression in murine colon cancer cells transduced with herpes simplex virus thymidine kinase gene", Cancer Gene Ther., 13:1093-104 (2006).
Kunte, et al., "Hemorrhagic transformation of ischemic stroke in diabetics on sulfonylureas", Ann Neurol., 72:799-806 (2012).
Li, et al., "Emerging drug targets for pain treatment", Eur J Pharmacol., 681:1-5 (2012).
Lieberman, "Screening for colorectal cancer", Clin Cornerstone, 4:1-10 (2002).
Liu, et al., "Metabolic profiling of murine plasma reveals an unexpected biomarker in rofecoxib-mediated cardiovascular events", PNAS.,, 107:17017-22 (2010).
Maddipati, et al., "Stability and analysis of eicosanoids and docosanoids in tissue culture media", Prostaglandins Other Lipid Mediat., 94:59-72 (2011).
Mu, et al., "Intravenous formulation of N-hydroxy-N'-(4-n-butyl-2-methylphenyl)formamidine (HET0016) for inhibition of rat brain 20-hydroxyeicosatetraenoic acid formation", Drug Metab Dispos., 36:2324-30 (2008).

(Continued)

*Primary Examiner* — Rei-Tsang Shiao
(74) *Attorney, Agent, or Firm* — Pabst Patent Group LLP

(57) ABSTRACT

Compositions containing one or more COX inhibitors in combination with one or more antagonists of 20-HETE (20-hydroxyeicosatetraeonic acid), and optionally a pharmaceutically acceptable excipient are provided. Preferred compositions include rofecoxib in combination with HET0016. The compositions have reduced side effects due to COX inhibitors. Methods for treating or inhibiting cancer using the disclosed compositions are also provided.

11 Claims, 11 Drawing Sheets

(56) References Cited

PUBLICATIONS

Muller, et al., "Mouse Cyp4a isoforms: enzymatic properties, gender- and strain-specific expression, and role in renal 20-hydroxyeicosatetraenoic acid formation", Biochem J., 403:109-18 (2007).

Nguyen, et al., "Kinetic profile of the rat CYP4A isoforms: arachidonic acid metabolism and isoform-specific inhibitors", Am J Physiol., 276:R1691-R1700 (1999).

Oyekan, "Differential effects of 20-hydroxyeicosatetraenoic acid on intrarenal blood flow in the rat", J Pharmacol Exp Ther., 313:1289-95 (2005).

Prakash, et al., "Enhanced cerebral but not peripheral angiogenesis in the Goto-Kakizaki model of type 2 diabetes involves VEGF and peroxynitrite signaling", Diabetes, 61:97 1533-42 (2012).

Regner, et al., "Protective effect of 20-HETE analogues in experimental renal ischemia reperfusion injury", Kidney Int., 75:511-7 (2009).

Reid, et al., "The human multidrug resistance protein MRP4 functions as a prostaglandin efflux transporter and is inhibited by nonsteroidal antiinflammatory drugs", PNAS., 100:9244-9 (2003).

Renic, et al., "Effect of 20-HETE inhibition on infarct volume and cerebral blood flow after transient middle cerebral artery occlusion", J Cereb Blood Flow Metab., 29: 629-39 (2009).

Roman, et al., "Evidence that 20-HETE contributes to the development of acute and delayed cerebral vasospasm", Neurol Res., 28: 738-49 (2006).

Roman, et al., "P-450 metabolites of arachidonic acid in the control of cardiovascular function", Physiol Rev., 82:131-85 (2002).

Schwartzman, et al., "Metabolism of 20-hydroxyeicosatetraenoic acid by cyclooxygenase. Formation and identification of novel endothelium-dependent vasoconstrictor metabolites", J Biol Chem., 264:11658-62 (1989).

Sheehan, et al., "The relationship between cyclooxygenase-2 expression and colorectal cancer", JAMA., 282: 1254-7 (1999).

Venkatesan, et al., "AEE788 potentiates celecoxib-induced growth inhibition and apoptosis in human colon cancer cells", Life Sci., 91:789-99 (2012).

Wang, et al., "Eicosanoids and cancer", Nat Rev Cancer, 10:181-93 (2010a).

Wang, et al., "The role of COX-2 in intestinal inflammation and colorectal cancer", Oncogene., 29:781-8 (2010b).

Yang, et al., "Attenuation of neonatal ischemic brain damage using a 20-HETE synthesis inhibitor", J Neurochem., 121: 168-79 (2012).

Yu, et al., "Cytochrome P450 É-hydroxylase promotes angiogenesis and metastasis by upregulation of VEGF and MMP-9 in non-small cell lung cancer", Cancer Chemother Pharmacol., 68: 619-29 (2011).

Yu, et al., "Effects of a 20-HETE antagonist and agonists on cerebral vascular tone", Eur J Pharmacol., 486:297-306 (2004).

Zarraga, et al., "Coxibs and heart disease: what we have learned and what else we need to know", J Am Coll Cardiol., 49:1-14 (2007).

\* cited by examiner

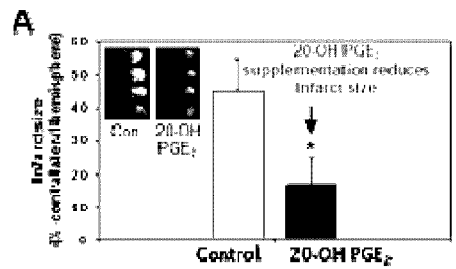
FIG. 9A
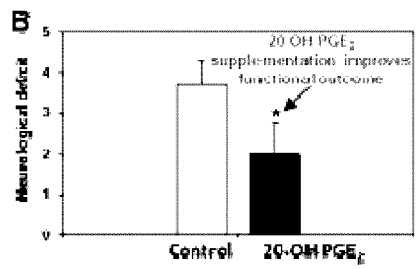
FIG. 9B
FIG. 10A and FIG. 10B
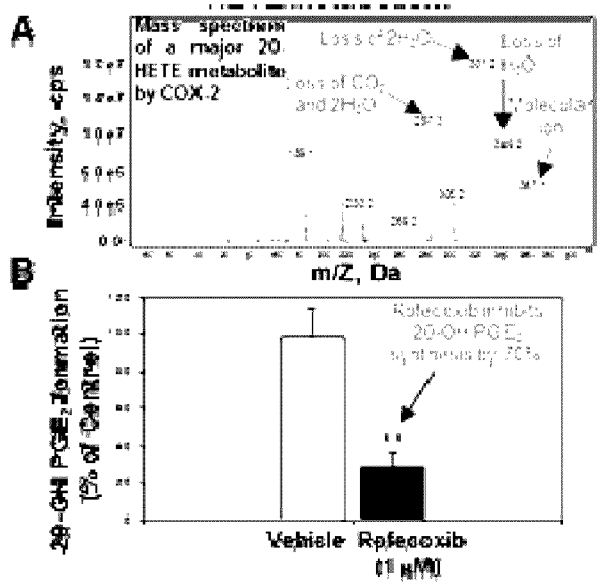

COMPOSITIONS AND METHODS FOR TREATING CANCER

CROSS REFERENCE TO RELATED APPLICATIONS

This application claims benefit of and priority to U.S. Provisional Patent Application No. 62/028,835 filed on Jul. 25, 2014, and is incorporated by reference in its entirety.

FIELD OF THE INVENTION

The field of the invention is generally directed to compositions and methods for treating cancer, in particular, colon cancer.

BACKGROUND OF THE INVENTION

Colorectal cancer (CRC) is a major public health problem because it is estimated that 142,820 new cases and 50,830 deaths from CRC in the United States in 2013 (National Cancer Institute website). Early detection and chemical prevention of CRC are two major strategies against it. Moreover, early management of premalignant lesions can significantly reduce CRC-related mortality (Lieberman, *Clin Cornerstone* 4: 1-10 (2002); Sheehan JAMA, 282: 1254-1257 (1999)). Coxibs (selective cyclooxygenase (COX-2 inhibitors) are the potential chemopreventive agents in the clinical trials because inflammation is associated with the development of CRC (Wang, et al., *Nat Rev Cancer* 10:181-193 (2010); Wang, et al., *Oncogene*, 29:781-788 (2010)).

Based on strong data that COX-2 is the major enzyme for the production of inflammatory $PGE_2$ (prostaglandin $E_2$) and $PGI_2$ (prostaglandin 12, also known as prostacylin) and that COX-1 is a key enzyme in the production of cytoprotective PGs (prostaglandins) in the stomach (Funk, et al., *J Cardiovasc Pharmacol*, 50: 470-479 (2007)), the Food and Drug Administration (FDA) has approved the use of three coxibs, rofecoxib, celecoxib, and valdecoxib. Clinically, nonsteroidal anti-inflammatory drugs (NSAIDs) are the primary choice for the treatment of inflammation (Li, et al., *Eur J Pharmacol* 681:1-5 (2012)). However, use of conventional NSAIDs is often associated with significant gastrointestinal complications such as ulcers and bleeding. Coxibs were developed to reduce the side effects of NSAIDs (FitzGerald, *N Engl J Med* 351:1709-1711 (2004)). While substantial evidence from clinical trials (APC, APPROVe, and PreSAP trial) demonstrates that coxibs reduce and prevent the incidence of CRC (Arber, et al., *Am J Gastroenterol* 106:1135-1146 (2011); Bertagnolli, et al., *N Engl J Med* 355: 873-884 (2006) and Bresalier, et al., *N Engl J Med* 352: 1092-1102 (2005)), long-term use of rofecoxib is also associated with an increased risk of side effects, including stroke and cardiovascular events (Bresalier, et al., *N Engl J Med* 352:1092-1102 (2005)). Consequently, rofecoxib (VIOXX®) and valdecoxib were withdrawn from the market; clinical trials of the use of rofecoxib were stopped in 2004. Currently, celecoxib (CELEBREX®), which is less potent than rofecoxib, is the only coxib on the market. Thus, the current unmet need in this field is to develop a new strategy that can not only enhance the efficacy of coxibs, but also reduce coxib-induced cerebrovascular damage.

It is an object of the present invention to provide compositions and methods which enhance the efficacy of coxibs and reduce coxib-induced cerebrovascular damage or coxib-related side effects.

It is also an object of the present invention to provide compositions and methods of treating cancer with coxibs that have reduced side effects due to coxib treatment.

It is still another object of the invention to provide compositions and methods for treating cancer with combination therapies that reduce the side effects due to coxib treatment.

SUMMARY OF THE INVENTION

Compositions containing one or more COX inhibitors in combination with one or more antagonists of 20-HETE (20-hydroxyeicosatetraeonic acid), and optionally a pharmaceutically acceptable excipient are provided. In some embodiments the COX inhibitor is selected from the group consisting of rofecoxib, celecoxib, cimicoxib, deracoxib, firocoxib, mavacoxib, robenacoxib, valdecoxib, parecoxib, etoricoxib. In a preferred embodiment, the composition includes rofecoxib and the 20-HETE antagonist is HET0016.

Also provided is a method of enhancing the therapeutic effect of a COX inhibitor and/or reducing side effects associated with administration of a COX inhibitor. The method includes administering a COX inhibitor in combination or alteration with one or more antagonists of 20-HETE to a subject in need thereof. The 20-HETE antagonist can be administered before, concurrently, or subsequent to administering the COX inhibitor. Side effects are selected from the group consisting of myocardial infarction, arterial and venous thrombic events, ischemic stroke, and arrhythmia Methods for treating cancer, reducing the risk of developing cancer, and for reducing the development of colorectal adenomas are also provided.

Another embodiment provides a method of reducing infarct size by administering an effective amount of 20-OH $PGE_2$.

BRIEF DESCRIPTION OF THE DRAWINGS

FIG. 9A is a vertical bar graph of m/z, Da versus intensity (cps) of 20-HETE metabolized by COX-2 into 20-OH $PGE_2$. FIG. 9B is a bar graph showing 20-OH $PGE_2$ formation (% of control) with vehicle or rofecoxib.

FIG. 10A is a bar graph showing Infarct size *(% control lateral hemisphere) for B6 mice treated with vehicle (control) or 20-OH PGE2 (250 ng/h in an osmotic pump). FIG. 10B shows neurological deficit for B6 mice treated with vehicle (control) or 20-OH PGE2 (250 ng/h in an osmotic pump).

DETAILED DESCRIPTION OF THE INVENTION

I. Definitions

Figure 1A:
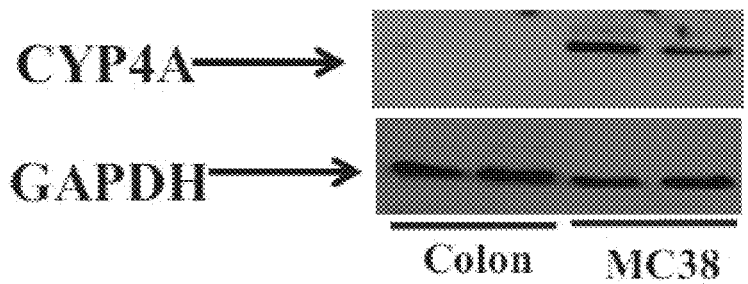
FIG. 1A is a representative Western blot analysis of Cyp4a in samples of normal mouse colon and MC38 cell lysate.

The term "coxib" refers to a cyclooxygenase-2 (COX-2) inhibitor.

The term "coxib-induced cerebrovascular damage" refers to damage caused by COX-2 inhibitors when administered to a subject. Such damage includes, but is not limited to myocardial infarction, arterial and venous thrombic events, ischemic stroke, and arrhythmia.

"Aerosol" as used herein refers to any preparation of a fine mist of particles, which can be in solution or a suspension, whether or not it is produced using a propellant.

"Amphiphilic" as used herein refers to a molecule combining hydrophilic and lipophilic (hydrophobic) properties.

A "continuous phase" refers to the liquid in which solids are suspended or droplets of another liquid are dispersed, and is sometimes called the external phase. This also refers to the fluid phase of a colloid within which solid or fluid particles are distributed. If the continuous phase is water (or another hydrophilic solvent), water-soluble or hydrophilic drugs will dissolve in the continuous phase (as opposed to being dispersed). In a multiphase formulation (e.g., an emulsion), the discreet phase is suspended or dispersed in the continuous phase.

A "cream" is a viscous liquid or semi-solid emulsion of either the "oil-in-water" or "water-in-oil type".

An "emulsion" is a composition containing a mixture of non-miscible components homogenously blended together.

"Gel" as used herein is a colloid in which the dispersed phase has combined with the continuous phase to produce a semisolid material, such as jelly.

"Hydrophilic" as used herein refers to substances that have strongly polar groups that readily interact with water.

"Hydrophobic" as used herein refers to substances that lack an affinity for water; tending to repel and not absorb water as well as not dissolve in or mix with water.

"Lipophilic" as used herein refers to compounds having an affinity for lipids.

A "lotion" is a low- to medium-viscosity liquid formulation.

"Oil" as used herein refers to a composition containing at least 95% wt. of a lipophilic substance. Examples of lipophilic substances include but are not limited to naturally occurring and synthetic oils, fats, fatty acids, lecithins, triglycerides and combinations thereof.

An "ointment" is a semisolid preparation containing an ointment base and optionally one or more active agents.

"Parenteral administration", as used herein, means administration by any method other than through the digestive tract or non-invasive topical or regional routes.

"Pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

"Pharmaceutically acceptable salt", as used herein, refers to derivatives of the compounds defined herein, wherein the parent compound is modified by making acid or base salts thereof.

"Therapeutically effective" or "effective amount" as used herein means that the amount of the composition used is of sufficient quantity to ameliorate one or more causes or symptoms of a disease or disorder. Such amelioration only requires a reduction or alteration, not necessarily elimination. As used herein, the terms "therapeutically effective amount" "therapeutic amount" and "pharmaceutically effective amount" are synonymous. One of skill in the art can readily determine the proper therapeutic amount.

A "subject" or "patient" refers to a human, primate, non-human primate, laboratory animal, farm animal, livestock, or a domestic pet.

II. Compositions

The compositions disclosed herein include one or more COX-2 selective inhibitors in combination with one or more 20-Hydroxyeicosatetraenoic acid (20-HETE) blockers. A preferred embodiment provides a pharmaceutical composition containing one or more COX-2 selective inhibitors in combination with one or more 20-HETE blockers optionally containing an excipient. The compositions can be formulated into unit dosage forms as well as packaged into multiple dosage forms, for example a blister pack containing multiple individual unit dosage forms.

A. Compounds

1. COX-2 Selective Inhibitors

A COX-2 selective inhibitor (coxib) is a form of non-steroidal anti-inflammatory drug (NSAID) that directly targets COX-2, an enzyme responsible for the transformation of arachidonic acid to prostaglandin H2 ($PGH_2$). Inhibition of COX-2 is used to treat a variety of pain syndromes (Zarraga et al., *J Am Coll Cardiol*, 49:1-14 (2007)). Representative coxibs that can be used in the compositions include, but are not limited to celecoxib (CELEBREX®), rofecoxib (VIOXX®), etoricoxib (ARCOXIA®) and valdecoxib (BEXTRA®). Thus, the compositions can contain one or more of the coxibs selected from the group consisting of celecoxib, rofecoxib, etoricoxib and valdecoxib. Preferred coxibs are those that induce 20-HETE production, for example rofecoxib. The compositions can contain 12.5, 25, 50, 100, 200 or 400 mg of one or more coxibs.

In certain embodiments, derivatives of coxibs can be used. Exemplary derivatives of coxibs include, but are not limited to two seleno-derivatives of celecoxib such as 4-[5-(4-methylphenyl)-3-(methylselenocyano)-1H-pyrazol-1-yl] benzene-sulfonamide (Selecoxib-CN), 4-[5-(4-(methylselenomethylene)phenyl)-3-(trifluoromethyl)-1H-pyrazol-1-yl] benzene-sulfonamide (Selecoxib-Me) and 2,5-dimethyl-celecoxib.

2. 20-HETE Antagonist

The compositions also contain one or more 20-HETE antagonists. Representative 20-HETE antagonists include, but are not limited to 20-hydroxyeicosa-6(Z),15(Z)-dienoic acid (WIT002), N-Hydroxy-N'-(4-butyl-2-methylphenyl) formamidine (HET0016), 17-octadecynoic acid (17-ODYA), N-methylsulfonyl-12,12-dibromododec-11-enamide (DDMS), dibromododec-11-enoic acid (DDBB), N-(3-Chloro-4-morpholin-4-yl)Phenyl-N'-hydroxyimido formamide (TS011).

In some embodiment, analogues of 20-HETE can be used. Exemplary analogues of 20-HETE that can be used include, but are not limited to 20-hydroxyeicosa-6(Z),15(Z)-dienoic acid (6-,15-,20-HEDE) and (N-[20-hydroxyeicosa-5 (Z), 14 (Z)-dienoic acid (5, 14, 20-HEDGE).

The disclosed compositions can include 12.5, 25, 50, 100, 200 or 400 mg of one or more of a 20-HETE antagonist.

A preferred embodiment provides a composition that includes rofecoxib and N-Hydroxy-N'-(4-butyl-2-methylphenyl)formamidine (HET0016) in an amount effective to kill cancer or tumor cells or to inhibit tumor growth. An effective amount of HET0016 includes an amount effective to reduce side effects due to rofecoxib administration, for example myocardial infarction, stroke or both. A preferred cancer is colon cancer.

B. Formulations

The compounds described herein are preferably formulated for enteral or parenteral administration. The compounds can be combined with one or more pharmaceutically acceptable carriers and/or excipients that are considered safe and effective and may be administered to an individual without causing undesirable biological side effects or unwanted interactions.

1. Enteral Formulations

Enteral administration refers to drug administration through the digestion process of a gastrointestinal (GI) tract. Enteral formulations include oral formulations. Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art.

Formulations may be prepared using a pharmaceutically acceptable carrier. As generally used herein "carrier" includes, but is not limited to, diluents, preservatives, binders, lubricants, disintegrators, swelling agents, fillers, stabilizers, and combinations thereof.

Carrier also includes all components of the coating composition, which may include plasticizers, pigments, colorants, stabilizing agents, and glidants.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

"Diluents", also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

"Binders" are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

"Lubricants" are used to facilitate tablet manufacture. Examples of suitable lubricants include, but are not limited to, magnesium stearate, calcium stearate, stearic acid, glycerol behenate, polyethylene glycol, talc, and mineral oil.

"Disintegrants" are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone® XL from GAF Chemical Corp).

"Stabilizers" are used to inhibit or retard drug decomposition reactions, which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

2. Controlled Release Enteral Formulations

Oral dosage forms can for formulated for controlled release. For example, the compounds containing a coxib and 20-HETE antagonist can be formulated into nanoparticles, microparticles, and combinations thereof, and optionally encapsulated in a soft or hard gelatin or non-gelatin capsule or dispersed in a dispersing medium to form an oral suspension or syrup. The particles can be formed of the drugs and a controlled release polymer or matrix. Alternatively, the drug particles can be coated with one or more controlled release coatings prior to incorporation in to the finished dosage form.

In another embodiment, the coxib and 20-HETE are dispersed in a matrix material which gels or emulsifies upon contact with an aqueous medium, such as physiological fluids. In the case of gels, the matrix swells entrapping the active agents, which are released slowly over time by diffusion and/or degradation of the matrix material. Such matrices can be formulated as tablets or as fill materials for hard and soft capsules.

In still another embodiment, the coxib and 20-HETE antagonist are formulated into a sold oral dosage form, such as a tablet or capsule, and the solid dosage form is coated with one or more controlled release coatings, such as a delayed release coatings or extended release coatings. The coating or coatings may also contain the compounds and/or additional active agents. Delayed or extended release coatings are known in the art and discussed below.

(a) Extended Release Dosage Forms

The extended release formulations are generally prepared as diffusion or osmotic systems, which are known in the art. A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly (methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the tradename EUDRAGIT t®. In further preferred embodiments, the acrylic polymer comprises a mixture of two acrylic resin lacquers commercially available from Rohm Pharma under the tradenames EUDRAGIT® RL30D and EUDRAGIT® RS30D, respectively. EUDRAGIT® RL30D and EUDRAGIT® RS30D are copolymers of acrylic and methacrylic esters with a low content of quaternary ammonium groups, the molar ratio of ammonium groups to the remaining neutral (meth)acrylic esters being 1:20 in EUDRAGIT® RL30D and 1:40 in EUDRAGIT® RS30D. The mean molecular weight is about 150,000. EUDRAGIT® S-100 and EUDRAGIT® L-100 are also preferred. The code designations RL (high permeability) and RS (low permeability) refer to the permeability properties of these agents. EUDRAGIT® RL/RS mixtures are insoluble in water and in digestive fluids. However, multiparticulate systems formed to include the same are swellable and permeable in aqueous solutions and digestive fluids.

The polymers described above such as EUDRAGIT® RL/RS may be mixed together in any desired ratio in order to ultimately obtain a sustained-release formulation having a desirable dissolution profile. Desirable sustained-release multiparticulate systems may be obtained, for instance, from 100% EUDRAGIT® RL, 50% EUDRAGIT® RL and 50% EUDRAGIT t® RS, and 10% EUDRAGIT® RL and 90% EUDRAGIT® RS. One skilled in the art will recognize that other acrylic polymers may also be used, such as, for example, EUDRAGIT® L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

(b) Delayed Release Dosage Forms

Delayed release formulations can be created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including EUDRAGIT® L30D-55 and L100-55 (soluble at pH 5.5 and above), EUDRAGIT® L-100 (soluble at pH 6.0 and above), EUDRAGIT® S (soluble at pH 7.0 and above, as a result of a higher degree of esterification), and EUDRAGITS® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

3 Parenteral Formulations

Parenteral administration refers to drug administration that occurs from routes outside the GI tract, such as intravenous routes. Parenteral administration may include administration to a patient intravenously, intradermally, intraarterially, intraperitoneally, intralesionally, intracranially, intraarticularly, intraprostatically, intrapleurally, intratracheally, intravitreally, intratumorally, intramuscularly, subcutaneously, subconjunctivally, intravesicularly, intrapericardially, intraumbilically, by injection, and by infusion.

Parenteral formulations can be prepared as aqueous compositions using techniques known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, viscosity modifying agents, and combination thereof.

Suitable surfactants may be anionic, cationic, amphoteric or nonionic surface-active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers.

Water-soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

4. Controlled Release Parenteral Formulations

The parenteral formulations described herein can be formulated for controlled release including immediate release, delayed release, extended release, pulsatile release, and combinations thereof (a). Nano- and Microparticles For parenteral administration, the one or more compounds, and optional one or more additional active agents, can be incorporated into microparticles, nanoparticles, or combinations thereof that provide controlled release of the compounds and/or one or more additional active agents. In embodiments wherein the formulations contains two or more drugs, the drugs can be formulated for the same type of controlled release (e.g., delayed, extended, immediate, or pulsatile) or the drugs can be independently formulated for different types of release (e.g., immediate and delayed, immediate and extended, delayed and extended, delayed and pulsatile, etc.).

For example, the compounds and/or one or more additional active agents can be incorporated into polymeric microparticles, which provide controlled release of the drug(s). Release of the drug(s) is controlled by diffusion of the drug(s) out of the microparticles and/or degradation of the polymeric particles by hydrolysis and/or enzymatic degradation. Suitable polymers include ethylcellulose and other natural or synthetic cellulose derivatives.

Polymers, which are slowly soluble and form a gel in an aqueous environment, such as hydroxypropyl methylcellulose or polyethylene oxide, can also be suitable as materials for drug containing microparticles. Other polymers include, but are not limited to, polyanhydrides, poly(ester anhydrides), polyhydroxy acids, such as polylactide (PLA), polyglycolide (PGA), poly(lactide-co-glycolide) (PLGA), poly-3-hydroxybutyrate (PHB) and copolymers thereof, poly-4-hydroxybutyrate (P4HB) and copolymers thereof, polycaprolactone and copolymers thereof, and combinations thereof.

Alternatively, the drug(s) can be incorporated into microparticles prepared from materials which are insoluble in aqueous solution or slowly soluble in aqueous solution, but are capable of degrading within the GI tract by means including enzymatic degradation, surfactant action of bile acids, and/or mechanical erosion. As used herein, the term "slowly soluble in water" refers to materials that are not dissolved in water within a period of 30 minutes. Preferred examples include fats, fatty substances, waxes, wax-like substances and mixtures thereof. Suitable fats and fatty substances include fatty alcohols (such as lauryl, myristyl stearyl, cetyl or cetostearyl alcohol), fatty acids and derivatives, including but not limited to fatty acid esters, fatty acid glycerides (mono-, di- and tri-glycerides), and hydrogenated fats. Specific examples include, but are not limited to hydrogenated vegetable oil, hydrogenated cottonseed oil, hydrogenated castor oil, hydrogenated oils available under the trade name Sterotex®, stearic acid, cocoa butter, and stearyl alcohol. Suitable waxes and wax-like materials include natural or synthetic waxes, hydrocarbons, and normal waxes. Specific examples of waxes include beeswax, glycowax, castor wax, carnauba wax, paraffins and candelilla wax. As used herein, a wax-like material is defined as any material, which is normally solid at room temperature and has a melting point of from about 30 to 300° C.

In some cases, it may be desirable to alter the rate of water penetration into the microparticles. To this end, rate-controlling (wicking) agents can be formulated along with the fats or waxes listed above. Examples of rate-controlling materials include certain starch derivatives (e.g., waxy maltodextrin and drum dried corn starch), cellulose derivatives (e.g., hydroxypropylmethyl-cellulose, hydroxypropylcellulose, methylcellulose, and carboxymethyl-cellulose), alginic acid, lactose and talc. Additionally, a pharmaceutically acceptable surfactant (for example, lecithin) may be added to facilitate the degradation of such microparticles.

Proteins, which are water insoluble, such as zein, can also be used as materials for the formation of drug containing microparticles. Additionally, proteins, polysaccharides and combinations thereof, which are water-soluble, can be formulated with drug into microparticles and subsequently cross-linked to form an insoluble network. For example, cyclodextrins can be complexed with individual drug molecules and subsequently cross-linked.

(b). Method of Making Nano- and Microparticles

In the case of enteral or parenteral formulations, encapsulation or incorporation of drug into carrier materials to produce drug-containing microparticles can be achieved through known pharmaceutical formulation techniques. In the case of formulation in fats, waxes or wax-like materials, the carrier material is typically heated above its melting temperature and the drug is added to form a mixture comprising drug particles suspended in the carrier material, drug dissolved in the carrier material, or a mixture thereof. Microparticles can be subsequently formulated through several methods including, but not limited to, the processes of congealing, extrusion, spray chilling or aqueous dispersion. In a preferred process, wax is heated above its melting temperature, drug is added, and the molten wax-drug mixture is congealed under constant stirring as the mixture cools. Alternatively, the molten wax-drug mixture can be extruded and spheronized to form pellets or beads. These processes are known in the art.

For some carrier materials it may be desirable to use a solvent evaporation technique to produce drug-containing microparticles. In this case drug and carrier material are co-dissolved in a mutual solvent and microparticles can subsequently be produced by several techniques including, but not limited to, forming an emulsion in water or other appropriate media, spray drying or by evaporating off the solvent from the bulk solution and milling the resulting material.

In some embodiments, drug in a particulate form is homogeneously dispersed in a water-insoluble or slowly water soluble material. To minimize the size of the drug particles within the composition, the drug powder itself may be milled to generate fine particles prior to formulation. The process of jet milling, known in the pharmaceutical art, can be used for this purpose. In some embodiments drug in a particulate form is homogeneously dispersed in a wax or wax like substance by heating the wax or wax like substance above its melting point and adding the drug particles while stirring the mixture. In this case a pharmaceutically acceptable surfactant may be added to the mixture to facilitate the dispersion of the drug particles.

The particles can also be coated with one or more modified release coatings. Solid esters of fatty acids, which are hydrolyzed by lipases, can be spray coated onto microparticles or drug particles. Zein is an example of a naturally water-insoluble protein. It can be coated onto drug containing microparticles or drug particles by spray coating or by wet granulation techniques. In addition to naturally water-insoluble materials, some substrates of digestive enzymes can be treated with cross-linking procedures, resulting in the formation of non-soluble networks. Many methods of cross-linking proteins, initiated by both chemical and physical means, have been reported. One of the most common methods to obtain cross-linking is the use of chemical cross-linking agents. Examples of chemical cross-linking agents include aldehydes (gluteraldehyde and formaldehyde), epoxy compounds, carbodiimides, and genipin. In addition to these cross-linking agents, oxidized and native sugars have been used to cross-link gelatin. Cross-linking can also be accomplished using enzymatic means; for example, transglutaminase has been approved as a GRAS substance for cross-linking seafood products. Finally, cross-linking can be initiated by physical means such as thermal treatment, UV irradiation and gamma irradiation.

To produce a coating layer of cross-linked protein surrounding drug containing microparticles or drug particles, a water-soluble protein can be spray coated onto the microparticles and subsequently cross-linked by the one of the methods described above. Alternatively, drug-containing microparticles can be microencapsulated within protein by coacervation-phase separation (for example, by the addition of salts) and subsequently cross-linked. Some suitable proteins for this purpose include gelatin, albumin, casein, and gluten.

Polysaccharides can also be cross-linked to form a water-insoluble network. For many polysaccharides, this can be accomplished by reaction with calcium salts or multivalent cations, which cross-link the main polymer chains. Pectin, alginate, dextran, amylose and guar gum are subject to cross-linking in the presence of multivalent cations. Complexes between oppositely charged polysaccharides can also be formed; pectin and chitosan, for example, can be complexed via electrostatic interactions.

5. Injectable/Implantable Formulations

The compounds described herein can be incorporated into injectable/implantable solid or semi-solid implants, such as polymeric implants. In one embodiment, the compounds are incorporated into a polymer that is a liquid or paste at room temperature, but upon contact with aqueous medium, such as physiological fluids, exhibits an increase in viscosity to form a semi-solid or solid material. Exemplary polymers include, but are not limited to, hydroxyalkanoic acid polyesters derived from the copolymerization of at least one unsaturated hydroxy fatty acid copolymerized with hydroxyalkanoic acids. The polymer can be melted, mixed with the active substance and cast or injection molded into a device. Such melt fabrication require polymers having a melting point that is below the temperature at which the substance to be delivered and polymer degrade or become reactive. The device can also be prepared by solvent casting where the polymer is dissolved in a solvent and the drug dissolved or dispersed in the polymer solution and the solvent is then evaporated. Solvent processes require that the polymer be soluble in organic solvents. Another method is compression molding of a mixed powder of the polymer and the drug or polymer particles loaded with the active agent.

Alternatively, the compounds can be incorporated into a polymer matrix and molded, compressed, or extruded into a device that is a solid at room temperature. For example, the compounds can be incorporated into a biodegradable polymer, such as polyanhydrides, polyhydroalkanoic acids (PHAs), PLA, PGA, PLGA, polycaprolactone, polyesters, polyamides, polyorthoesters, polyphosphazenes, proteins and polysaccharides such as collagen, hyaluronic acid, albumin and gelatin, and combinations thereof and compressed into solid device, such as disks, or extruded into a device, such as rods.

The release of the one or more compounds from the implant can be varied by selection of the polymer, the molecular weight of the polymer, and/or modification of the polymer to increase degradation, such as the formation of pores and/or incorporation of hydrolyzable linkages. Methods for modifying the properties of biodegradable polymers to vary the release profile of the compounds from the implant are well known in the art.

III. Methods of Use

One embodiment provides a method for inhibiting tumor growth in a subject in need thereof by administering a combination of one or more coxibs and one or more 20-HETE antagonists to a subject in need thereof. The coxib and 20-HETE antagonist can be administered simultaneously or in alternation, wherein the 20-HETE antagonist is administered in an amount and frequency to inhibit or reduce side effects caused by the administration of the coxib. In a preferred embodiment, the 20-HETE antagonist is administered in an amount and frequency to reduce the risk of coxib-related myocardial infarction, coxib-related ischemic stroke, or both. The disclosed combination therapy can be administered with an additional therapeutic agent including but not limited to chemotherapy drugs or other drugs for the treatment of cancer or for the palliative treatment of a side effect of the administration of the chemotherapy drug. A preferred combination includes rofecoxib and HET0016.

In other embodiments, the coxib and 20-HETE antagonist are administered to a subject in need thereof to inhibit or reduce the growth and advancement of cancer or tumor cells in the subject.

Another embodiment provides administering the combination of coxib and 20-HETE antagonist to reduce the rate of recurrence of colorectal cancer in a subject.

Still another embodiment provides a method of reducing the risk of developing colorectal adenomas, or polyps, in a subject by administering a combination of coxib and 20-HETE antagonist to the subject.

In one embodiment, the combination of coxib and 20-HETE antagonist is administered to the subject after removal of one or more colorectal polyps from the subject.

The cancers that can be treated include, but are not limited to colorectal cancer, pancreatic cancer, lung cancer, kidney cancer, and brain cancer or tumors.

In another embodiment, the coxib and 20-HETE antagonist are administered separately. For example, the 20-HETE antagonist can be administered to a subject prior to administering a coxib or following the administration of a coxib. In a preferred embodiment, the coxib and 20-HETE antagonist are administered concurrently, simultaneously, or together.

Another method of treatment provides a method for reducing the side-effects of coxib treatment by administering to a subject in need thereof an effective amount of a 20-HETE antagonist. The side effects due to coxib treatment include, but are not limited to one or more of the following: myocardial infarction, arterial and venous thrombic events, ischemic stroke, and arrhythmia Still another embodiment provides a method of reducing infarct size by administering an effective amount of 20-OH $PGE_2$.

Yet another embodiment provides a method of reducing cerebral injury and improving functional recovery after stroke by administering to a subject in need thereof an effective amount of 20-OH $PGE_2$. In one embodiment, 20-OH $PGE_2$ is administered to a subject at risk of having a stroke prior to the subject having a stroke. 20-OH $PGE_2$ can be administered for days, weeks, or months prior to a stroke.

EXAMPLES

Statistical Analysis

All values are expressed as means±SE. All data were analyzed by GraphPad Instat Software (LaJolla, Calif.). One-way ANOVA and Tukey-Kramer tests for multiple comparisons or Independent Student's t test for unpaired groups were used. Bleeding was analyzed by Fisher's exact test. Statistical significance was set at P<0.05 or 0.01.

Example 1

Cyp4a Expression and 20-HETE Production in MC38 Cells

Materials and Methods
Animals
Eight-week-old male C57BL/6 mice were purchased from Jackson Laboratory (Bar Harbor, Me.). All mice were maintained on a 12:12-h light-dark cycle and were housed 5 mice to a cage. All animal protocols were approved by the Institutional Animal Care and Use Committee and were in accord with the requirements of the National Research Council Guide for the Care and Use of Laboratory Animals.

Cell Culture of MC38 Cells, HCMECL, and RBMECL

MC38 cells were maintained in complete medium consisting of DMEM supplemented with 10% heat-inactivated FBS, 100 mg/ml streptomycin, and 100 U/ml penicillin in a humidified incubator at 37° C. with 5% $CO_2$. Sub-confluent cultured cells were harvested by washing T-75 flasks two times with $Ca^{2+}$- and $Mg^{2+}$-free Earl's balanced salts, followed by 2 min incubation with 0.25% trypsin-EDTA (Life Technologies, Grand Island, N.Y.) at 37° C. A human cerebral microvascular endothelial cell line (HCMECL) was used in the studies (University of Georgia, Athens, Ga.). Primary rat brain microvascular endothelial cells (RBMEC) were prepared as described previously (Prakash, et al., *Diabetes* 61:97 1533-1542 (2012)). HCMECL and RBMEC were maintained in MCDB-131 complete medium (VEC Technologies, Rensselaer, N.Y.).

Western Blot Analysis

Expression of Cyp4a, COXs, β-actin, and GADPH (glyceraldehyde 3-phosphate dehydrogenase) was analyzed by Western blot analysis using the lysates of MC38 cells, HCMECL, and RBMEC as well as homogenates of mouse brain microvessels (MBM) and normal mouse colon samples. Identical amounts of protein samples were separated by NuPAGE 4%-12% Bis-Tris gel (Invitrogen, Carlsbad, Calif.) at 125 volts for 3 h. We have previously described the detailed procedures for transfer, blocking, and washing the samples (Chen, et al., *Prostaglandins Other Lipid Mediat* 104-105:42-48 (2013)). The membranes were incubated with antibody against Cyp4a polyclonal antibody (1:2,000; Abcam (Catalog #: ab3573), Cambridge, Mass.), COX-1 (1:500; Cayman Chemical (Catalog #: 160110), Ann Arbor, Mich.), COX-2 (1:500; Cayman Chemical (Catalog #: 160106), Ann Arbor, Mich.), β-actin (1:5,000; Sigma, St. Louis, Mo.), or GAPDH (1:10,000; Abcam (Catalog #: ab8245), Cambridge, Mass.). According to the manufacturer's instruction, this Cyp4a antibody can recognize human, rat, and mouse Cyp4a isoforms. Similarly, the COX-1 and COX-2 antibody can recognize human, rat, and mouse COX-1 and COX-2, respectively. The membranes were incubated with secondary antibody for Cyp4a, COX-1, COX-2, β-actin, or GAPDH. We developed the immunoblots using an ECL detection kit (GE Healthcare, Little Chalfont, Buckinghamshire, UK).

Measurement of 20-HETE and $PGE_2$ Levels in the Media and Cell Lysates of MC38 Cells MC38 cells were collected using 0.25% trypsin-EDTA. After centrifugation, a cell pallet was re-suspended in 300 µl of PBS. Cell lysates were generated by brief sonication. The concentrations of 20-HETE in media and cell lysates were determined by Liquid Chromatography—Tandem Mass Spectrometry (LC/MS/MS) using 15(S)-HETE-d8 as an internal standard as described previously (Chen, et al., *Prostaglandins Other Lipid Mediat* 104-105:42-48 (2013)). The media and cell lysates were collected for $PGE_2$ measurement. The concentrations of $PGE_2$ in media and cell lysates were determined by an ELISA kit (Cayman Chemical, Ann Arbor, Mich.) according to the manufacturer's instructions.

Results

It is well established that Cyp4a isoforms are important for the production of 20-HETE (Roman, et al., *Physiol Rev* 82:131-185 (2002)). To determine whether MC38 (murine colon carcinoma) cells have the capacity to synthesize 20-HETE, cell lysates were prepared from MC38 cells for Western blot analysis. Normal mouse colon tissue homogenates were used as a control. Assay for the expression of Cyp4a revealed intriguingly, that expression of Cyp4a is absent in normal colon tissue, whereas its expression is up-regulated in MC38 cells (FIG. 1A).

Figure 1B:
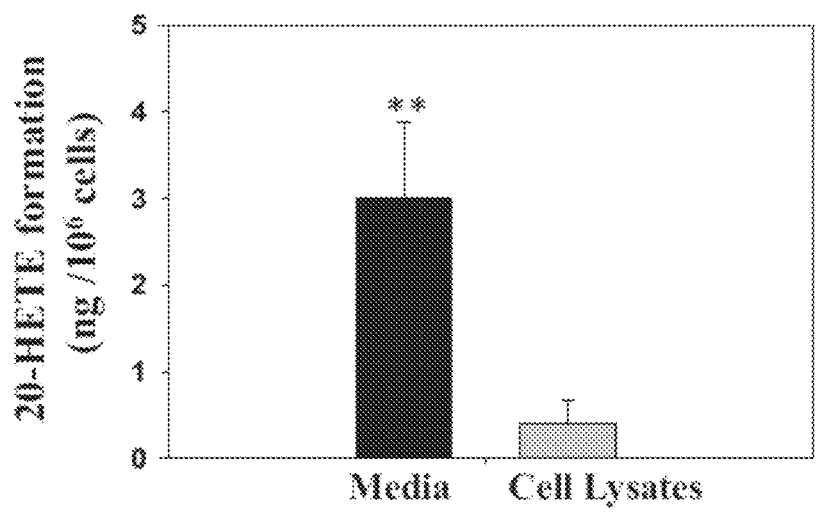
FIG. 1B shows 20-HETE (20-hydroxyeicosatetraeonic acid) levels in cell culture media and cell lysates of MC38 cells.
Figure 1C:
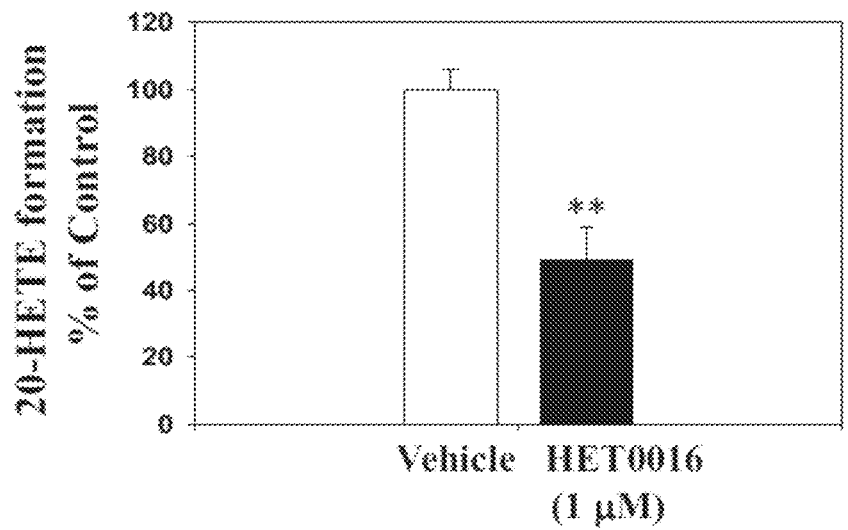
FIG. 1C shows the effect of HET0016 (N-hydroxy-N'-(4-n-butyl-2-methylphenyl)Formamidine) on 20-HETE production in MC38 cell media, and results are expressed as % control. 20-HETE levels were determined by LC/MS/MS. n=4. The results are expressed as the mean±SE.**P<0.01 versus control.

20-HETE levels were determined in the lysates and media of cultured MC38 cells. 20-HETE was detected predominantly in the cell media. Much lower amounts were found in cell lysates (FIG. 1B). To determine the effect of HET0016 (the selective inhibitor of Cyp4a enzymes) on 20-HETE production, MC38 cells were incubated with HET0016 (1 µM) or vehicle. HET0016 is a selective inhibitor of Cyp4a enzymes. HET0016 effectively blocked 20-HETE production and secretion in the media of cultured MC38 cells (FIG. 1C).

Example 2

COX-2 Expression and $PGE_2$ Production in MC38 Cells

Results

Figure 2A:
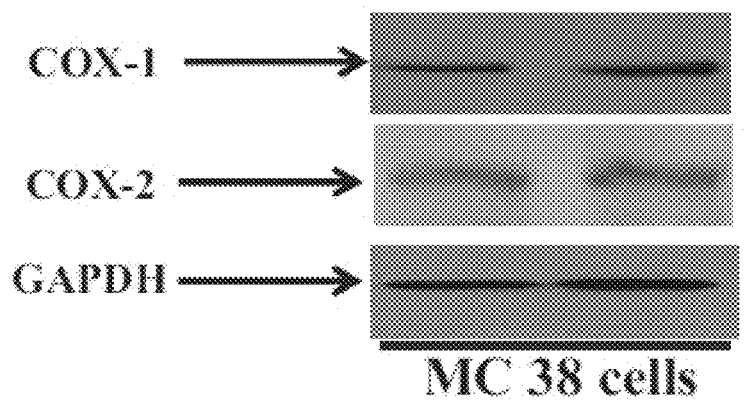
FIG. 2A is representative Western blot analysis of COXs (cyclooxygenases) in the lysates of MC38 cells.
Figure 2B:
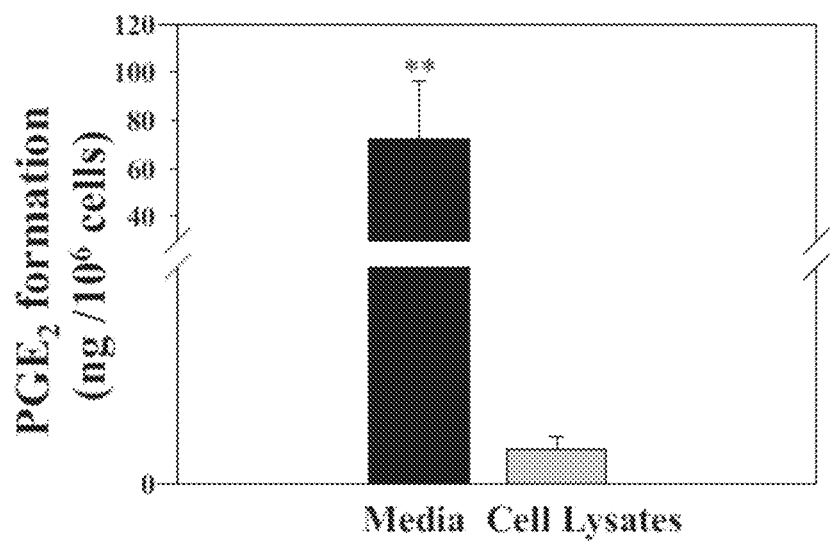
FIG. 2B shows PGE2 (prostaglandin E2) levels in cell culture media and in cell lysates of MC38 cells.
Figure 2C:
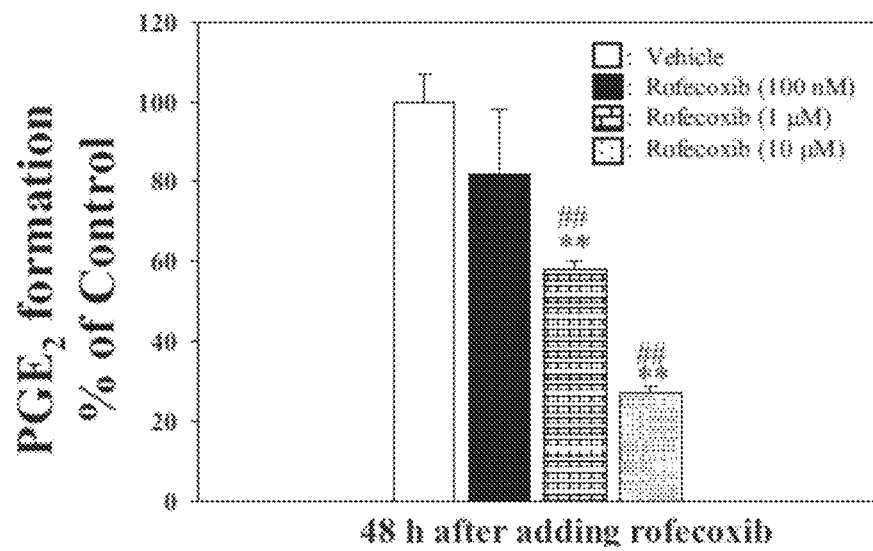
FIG. 2C shows the effect of rofecoxib on PGE2 production in MC38 cells, and results are expressed as % control. PGE2 production was estimated by a PGE2 ELISA. n=5. The results are expressed as the mean±SE.**P<0.01 versus cell lysates; ##P<0.01 versus other groups.

To determine whether MC38 cells have the capacity to generate PGs, Western blot analysis of COXs enzymes in the lysates of MC38 cells was performed. MC38 cell lysates contained a 72-kDa protein that cross-reacted with COX-2 antibody (FIG. 2A), which is in agreement with a previous report that COX-2 is expressed in MC38 cells (Konson, et al., *Cancer Gene Ther* 13:1093-1104 (2006)). Similarly, COX-1 is also expressed in MC38 cells. Experiments were also done to compare $PGE_2$ production in MC38 cells. $PGE_2$ was detected mainly in the media of cultured MC38 cells (72 ng/106 cells in the media versus 0.8 ng/106 cells in cell lysates) (FIG. 2B). Moreover, it was found that rofecoxib dose-dependently inhibited $PGE_2$ production in MC38 cells (FIG. 2C), indicating that rofecoxib effectively blocks PGs synthesis in these cells.

Example 3

Combination of Rofecoxib with HET0016 Causes an Additive Inhibitory Effect on the Growth and Proliferation of MC38 Cells Materials and Methods Measurement of Cell Proliferation of MC38 Cells by BrdU ELISA Assay MC38 cells were seeded at a density of $5 \times 10^3$ cells/well in 10% FBS/DMEM in 96-well plates. The next day, 10% FBS/DMEM medium was removed, and replaced with serum-free medium containing EGF (200 ng/ml) in the presence or absence of various concentrations of HET0016, rofecoxib, or HET0016+rofecoxib for 48 h. BrdU ELISA assay was done using an ELISA kit (CycLex Co., Nagano, Japan). Briefly, 3 h before assay, BrdU (10 µM final concentration) was added to the 96-well plates containing MC38 cells given different incubation conditions. After 3 h of incubation, the culture medium was removed, and fixed with Fixing/Denaturing solution (200 µl/well) at room temperature for 30 min. After removing Fixing/Denaturing solution, plates were incubated with monoclonal anti-BrdU antibody (50 µl/well) at room temperature for 1 h. Plates were washed five times with Wash buffer (200 µl/well), then incubated with the secondary antibody (50 µl/well) at room temperature for 1 h. After removing the secondary antibody and doing a second wash procedure, plates were incubated with Substrate Reagent (50 µl/well) at room temperature for 15 min in the dark. The reaction was then stopped by adding Stop Solution (50 µl/well). The absorbance in each well was measured using a Tecan GENios Plus microplate reader at dual wavelengths of 450/540 nm.

Measurement of Cell Proliferation of MC38 Cells by Counting Cell Numbers

For cell growth experiments, cells were seeded onto 6-well plates at a density of $2.5 \times 10^5$ cells/well. Cell growth of MC38 was followed 48 h after seeding with serum-free medium containing epidermal growth factor (EGF) (200 ng/ml) in the presence or absence of various concentrations of HET0016 (Cayman Chemical, Ann Arbor, Mich.), rofecoxib (Toronto Research Chemicals), or HET0016'rofecoxib. HET0016 and rofecoxib were dissolved in EtOH; an equal volume of EtOH, which did not exceed 0.1%, was used as vehicle control. After 48 h of treatment, cells were collected using 0.25% trypsin-EDTA and counted using a hemocytometer.

Results

It is well known that HET0016 avidly binds to serum proteins (Guo, et al., *J Pharmacol Exp Ther* 317:97-108 (2006)). To determine whether HET0016 alters the inhibitory effects of rofecoxib on the proliferation of colon cancer cells, MC38 cells were cultured in serum-free medium. The growth of these cells was stimulated with EGF, a mitogen of many cells, at a concentration of 200 ng/ml, as described previously ((Guo, et al., *J Pharmacol Exp Ther* 317:97-108 (2006)). Using the same culture conditions as those described earlier, both HET0016 alone (FIG. 3A) and rofecoxib alone (FIG. 3B) inhibited cell growth as measured using cell counting (using a hemocytometer). Interestingly, combining rofecoxib (1 µM) with HET0016 (1 µM) increased the inhibitory effect on the growth of MC38 cells as compared with rofecoxib alone (FIG. 3C).

Figure 4A:
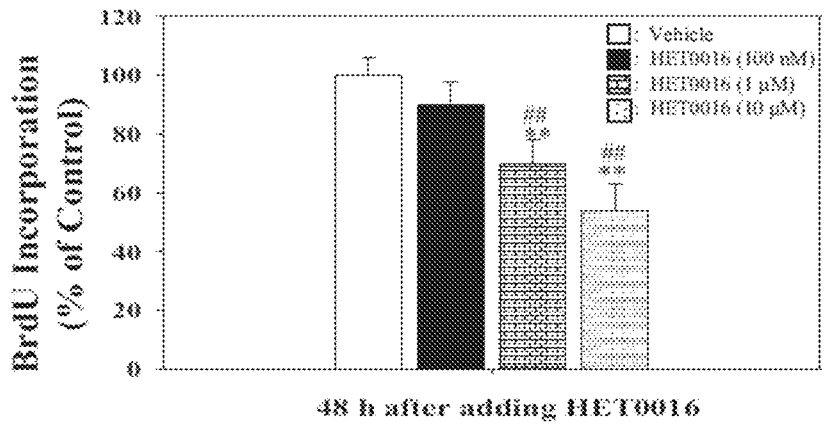
FIGS. 4A-C show the effects of HET0016, rofecoxib, and rofecoxib+HET0016 on BrdU incorporation into MC38 cells. MC38 cells growing in 96-well plates were treated with (FIG. 4A) HET0016 (100 nM to 10 μM), (FIG. 4B) rofecoxib (100 nM to 10 μM), or (FIG. 4C) HET0016 (1 μM)+rofecoxib (1 μM) for 48 h. In the last 3 h, BrdU was added (10 μM final concentration). Incorporation of BrdU was determined using an ELISA kit. Results are expressed as % control and are mean±SE. n=5. **$P<0.01$ versus vehicle; ##$P<0.01$ versus other groups.
Figure 4B:
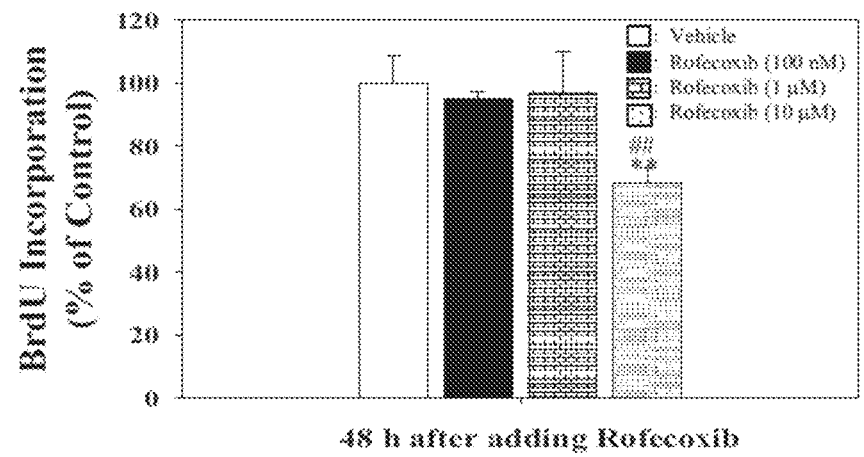
Figure 4C:
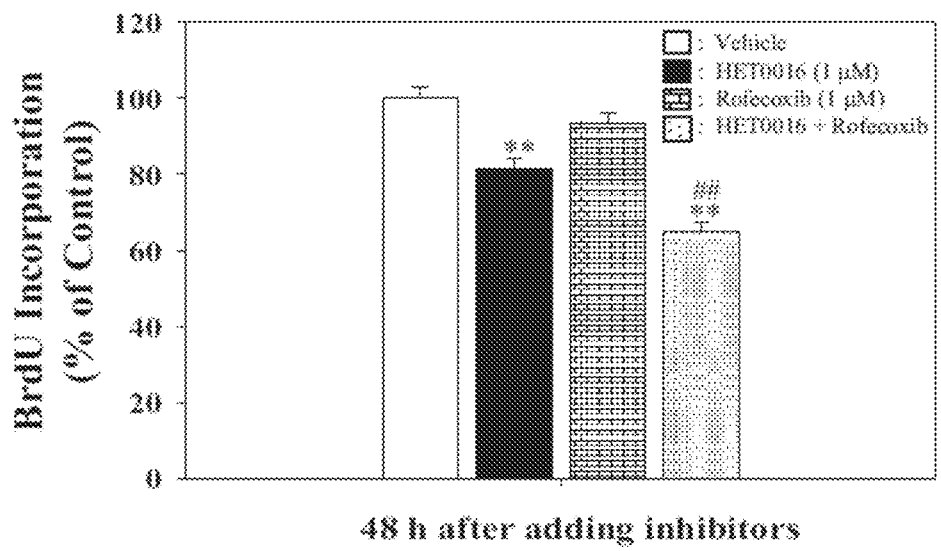

To confirm the effects of rofecoxib and HET0016 on the proliferation of colon cancer cells, MC38 cells were cultured in serum-free medium with added EGF (200 ng/ml). The effects of HET0016 alone, rofecoxib alone, and HET0016+ rofecoxib on the proliferation of MC38 cells were determined by assessing the incorporation of a thymidine analogue, bromodeoxyuridine (BrdU). HET0016 alone inhibited the incorporation of BrdU in a concentration dependent manner (FIG. 4A). Rofecoxib at 1 µM significantly inhibited BrdU incorporation (FIG. 4B). Notably, HET0016 (1 µM)+rofecoxib (1 µM), compared with rofecoxib alone, displayed an enhanced inhibitory effect on BrdU incorporation (FIG. 4C). These results demonstrate that inhibition of 20-HETE enhances the inhibitory effect of rofecoxib on the proliferation of MC38 cells.

Example 4

Inhibition of 20-HETE Enhances Anti-Tumor Effects of Rofecoxib in MC38 Colon Tumor-Bearing Mice Materials and Methods Measurement of Tumor Growth In Vivo 8-week-old male C57BL/6J mice were subcutaneously injected with MC38 cells (1.4×106 cells/mouse) to induce colon tumor. MC38 colon tumor-bearing mice were divided into vehicle, HET0016 (5 mg/kg/day or 10 mg/kg/day, i.p.), rofecoxib (50 mg/1 in drinking water), or HET0016+rofecoxib. All treatments were done for 21 days. Rofecoxib (50 mg/l) was suspended in drinking water containing 1% (vol/vol) PEG 400 (Sigma-Aldrich) and 0.5% (wt/vol) 2-hydroxypropyl-β-cyclodextrin (Sigma-Aldrich). The formula and dose of rofecoxib were prepared according to a previous publication (Liu, et al., *Proc Natl Acad Sci USA* 107: 17017-17022 (2010)). Tumor growth rates were monitored by measuring tumor volume with a sliding caliper on day 9 or day 18 after cell-implantation. The volumes of tumors were calculated from the major dimension (L) and minor dimension (S), using the equation: tumor volume=L×(S)2/2 as described previously (Konson, et al., *Cancer Gene Ther* 11: 830-840 (2004)).

Results

Figure 5A:
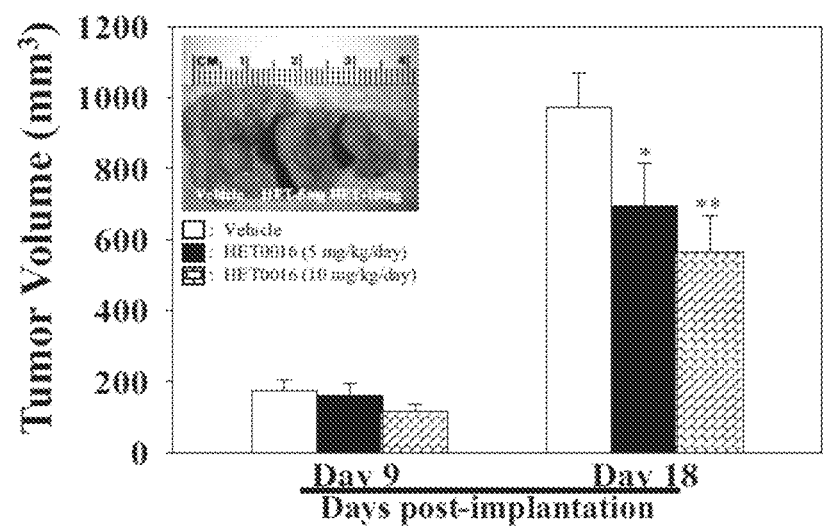
FIG. 5A shows the dose effects of HET0016 treatment on subcutaneous MC38 tumors in C57BL/6 mice.
Figure 5B:
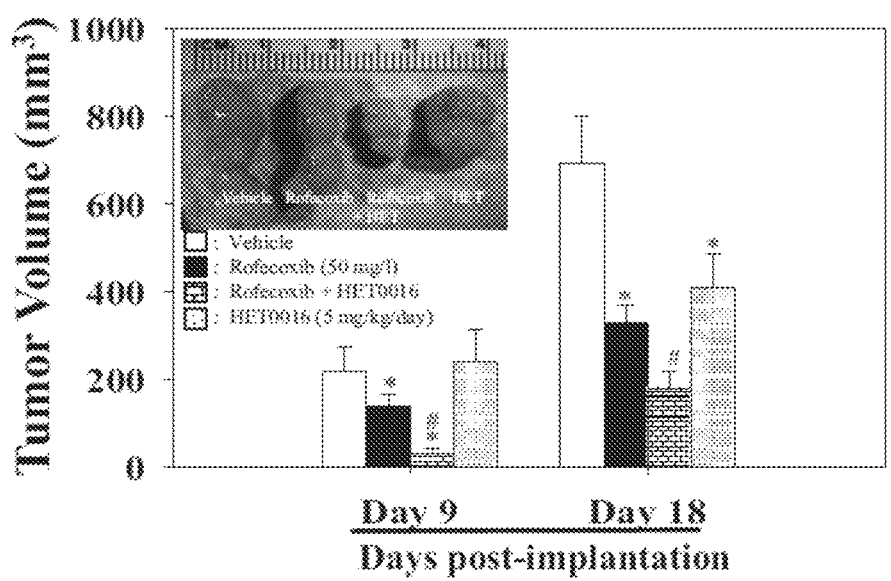
FIG. 5B shows the effects of rofecoxib+HET0016 on tumor growth in MC38 tumor mice which were divided into vehicle, rofecoxib (50 mg/l), HET0016 (5 mg/kg/day, i.p.), or rofecoxib+HET0016 treatment groups. n=6. *$P<0.05$, **$P<0.01$ versus vehicle; #$P<0.05$ versus other groups.

To study the effects of combination therapy with rofecoxib and HET0016 on colon tumor, 8-week-old male C57BL/6J mice were subcutaneously injected with MC38 cells ($1.4 \times 10^6$ cells/mouse) to induce colon tumor. The effects of HET0016 alone, rofecoxib alone, and HET0016+ rofecoxib on tumor growth were determined by assessing tumor volumes at 9 days and 18 days after the implantation of MC38 cells. Treatment with HET0016 did not affect tumor size on day 9 post implantation, but dose-dependently reduced tumor size on day 18 post-implantation (FIG. 5A). Treatment with rofecoxib significantly reduced tumor size on both day 9 and day 18 post-implantation (FIG. 5B). Interestingly, on days 9 and 18 post-implantation, treatment with HET0016+rofecoxib increased the inhibition of tumor growth achieved with rofecoxib alone (FIG. 5B), clearly demonstrating that inhibition of 20-HETE enhances the anti-tumor efficacy of rofecoxib in MC38 tumor-bearing mice.

In a complementary experiment, the water intake and body weight of mice treated with water, vehicle, and rofecoxib (50 mg/l) was determined. Neither vehicle (3.02±0.17 vs. 3.16±0.16 ml/24 h/mouse, n=5) nor rofecoxib (3.07±0.1 vs. 3.16±0.16 ml/24 h/mouse, n=5) treatment affected water intake. Likewise, there was no significant change of body weight among water (24±1.63 g/mouse, n=5), vehicle (23.8±1.1 g/mouse, n=5), and rofecoxib (24.5±1.0 g/mouse, n=5) group. These results indicate that neither vehicle nor rofecoxib treatment had significant impact on eating/drinking habits of treated mice.

Example 5

Prolonged Treatment with Rofecoxib Selectively Increases Circulating 20-HETE Levels in MC38 Colon Tumor-Bearing Mice Materials and Methods Measurement of 20-HETE and Other Eicosanoids in Plasma Samples by LC/MS/MS Analysis MC38 tumor mice were divided into three treatment groups and treated for 3 weeks with: rofecoxib (50 mg/l), rofecoxib (50 mg/l) plus HET0016 (5 mg/kg/day, i.p.), or vehicle. The formula and doses of rofecoxib and HET0016 were based on previous publications (Liu, et al., *Proc Natl Acad Sci USA* 107: 17017-17022 (2010); Mu, et al., *Drug Metab Dispos* 36:2324-2330 (2008)). After 3 weeks of different treatments, MC38 tumor mice were anesthetized with 2% isoflurane delivered by an anesthesia apparatus. About 0.6 ml of venous blood was collected from mice using a 1-ml syringe containing sodium citrate. The samples were centrifuged at 2,400×g for 15 min to obtain platelet-free plasma. To stabilize eicosanoids in plasma samples, 10 µl combinations of antioxidants (EDTA (0.2 mg/l), butylated hydroxytoluene (0.2 mg/l), and triphenyphosphine (2 mg/l)) were added to each plasma sample. The plasma samples were stored at −80° C. until LC/MS/MS analysis. Plasma samples were spiked with 10 ng of 15(S)-HETE-d8, applied to preconditioned SEP Pak C18 cartridges (100 mg adsorbent, Waters), and washed with water followed by hexane. Eicosanoids were eluted with 500 µl of ethyl acetate-hexane (3:1). The eluate was dried under nitrogen and reconstituted in methanol: 25 mM aqueous ammonium acetate (7:3). The extracted and reconstituted sample was subjected to HPLC (Shimadzu Prominence XR system) on a Max-RP C18 column (2×150 mm, 3 µu, Phenomenex) isocratically eluted with methanol:13 mM aqueous ammonium acetate (8:2) at a flow rate of 0.4 ml/min. The eluent was monitored for 20-HETE, EETs (5,6-EET, 8,9-EET, 11,12-EET, 14,15-EET), DHETs (5,6-DHET, 8,9-DHET, 11,12-DHET, 14,15-DHET), 5-HETE, 8-HETE, 11-HETE, 15-HETE, PGJ2, PGE2, TXB2, and 15keto-PGE2 by mass spectrometer (QTRAP5500, ABSCIEX) in the negative ion mode using Multiple Reaction Monitoring under optimized conditions. 15(S)-HETE-d8 was used as the internal standard for recovery and quantitation. The concentrations of eicosanoids were determined by comparing the ratio of ion intensity of each eicosanoid versus that of 15(S)-HETE-d8, as described previously (Chen, et al., *Prostaglandins Other Lipid Mediat* 104-105:42-48 (2013); Maddipati, et al., *Prostaglandins Other Lipid Mediat* 94:59-72 (2011)).

Results

Figure 6A:
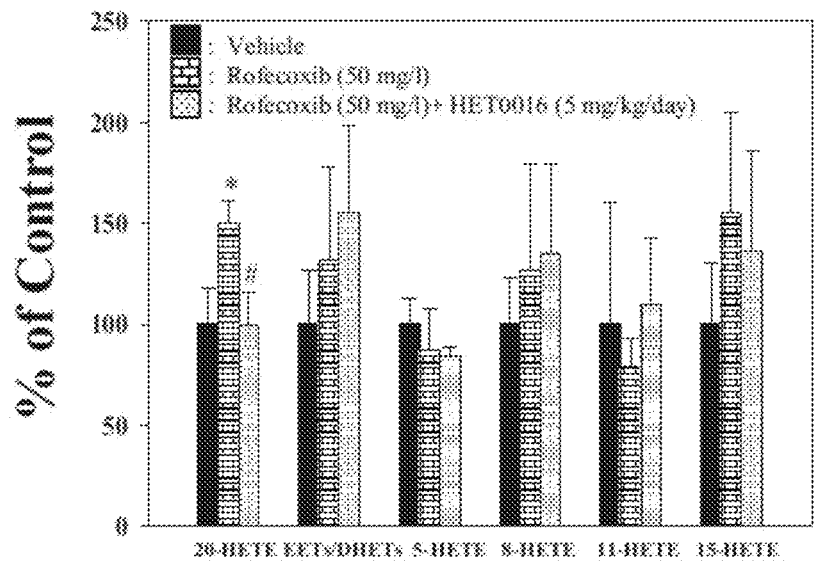
FIG. 6A shows plasma levels of 20-HETE, EETs (epoxyeicosatrienoic acids)/DHETs (dihydroxyeicosatrienoic acids), and other HETEs (hydroxyeicosatetraeonic acids) in MC38 colon tumor-bearing mice which were divided into 3 treatment groups: vehicle, rofecoxib (50 mg/l), or rofecoxib+HET0016 (5 mg/kg/day, i.p.).
Figure 6B:
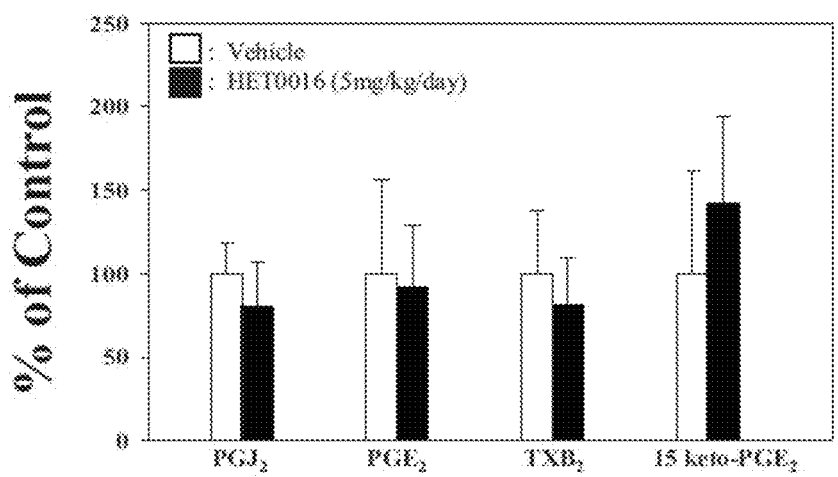
FIG. 6B shows the levels of plasma PGs in MC38 colon tumor-bearing mice which were treated with HET0016 (5 mg/kg/day, i.p.) or vehicle for 3 weeks.
Figure 6C:
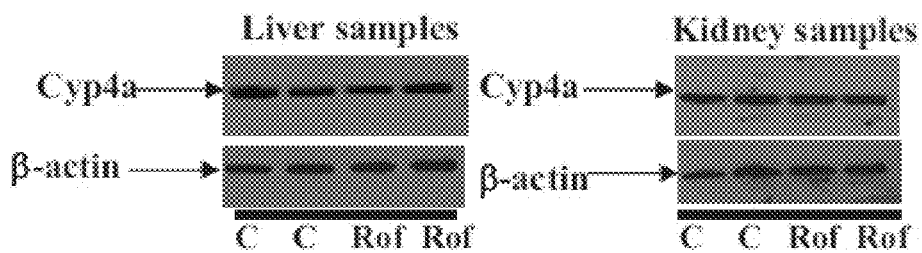
FIG. 6C shows the effects of 3-week treatment of rofecoxib on Cyp4a expression in the liver and kidney of MC38 tumor mice. C=control; Rof=rofecoxib treatment. *$P<0.05$ versus vehicle; #$P<0.05$ versus rofecoxib group.

To determine whether treatment with rofecoxib and rofecoxib+HET0016 affects circulating 20-HETE levels during anti-tumor therapy, the levels of plasma 20-HETE and other eicosanoids in MC38 tumor mice given different treatments, were measured. As shown in FIG. 6, rofecoxib selectively increased 20-HETE plasma levels in MC38 tumor mice. It is possible that the increased 20-HETE levels were caused by elevation of the substrate, AA (arachidonic acid), after blocking COX-2. However, no significant changes in levels of EETs/DHETs, 5-HETE, 8-HETE, 11-HETE, or 15-HETE were found after rofecoxib treatment (FIG. 6A). Notably, HET0016 selectively reduced plasma 20-HETE levels without affecting EETs/DHETs, 5-HETE, 8-HETE, 11-HETE, or 15-HETE in MC38 tumor mice (FIG. 6A). To exclude that HET0016 affects COX-pathway, plasma PGs levels we determined after HET0016 treatment. HET0016 did not affect plasma $PGJ_2$ (prostaglandin J2), $PGE_2$, TXB2 (thromboxane B2), and 15 keto-$PGE_2$ levels (FIG. 6B), suggesting that HET0016 does not alter COX-pathway in vivo. These results demonstrate that prolonged treatment with rofecoxib selectively induces circulating 20-HETE levels. To exclude the possibility that rofecoxib affects the expression of 20-HETE synthesizing enzyme, the expression of cyp4a in the liver and kidney was determined. Rofecoxib had no effect on cyp4a expression (FIG. 6C), suggesting that rofecoxib does not affect 20-HETE levels through altering the expression of cyp4a levels.

Example 6

Expression of COX-1, COX-2, and Cyp4a in HCMECL, Primary RBMEC, and MBM

Results

Figure 7A:
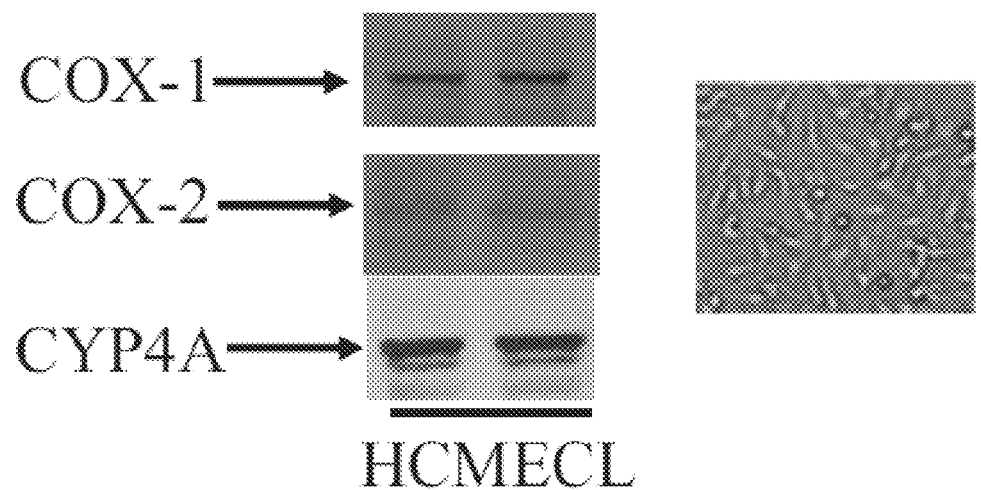
FIGS. 7A-C show expression of COX-1, COX-2, and CYP4A in HCMECL (FIG. 7A), RBMEC (FIG. 7B), and mouse BM (FIG. 7C). Microscopic images shown in the right of panel A and B are views of cultured HCMECL and RBMEC.
Figure 7B:
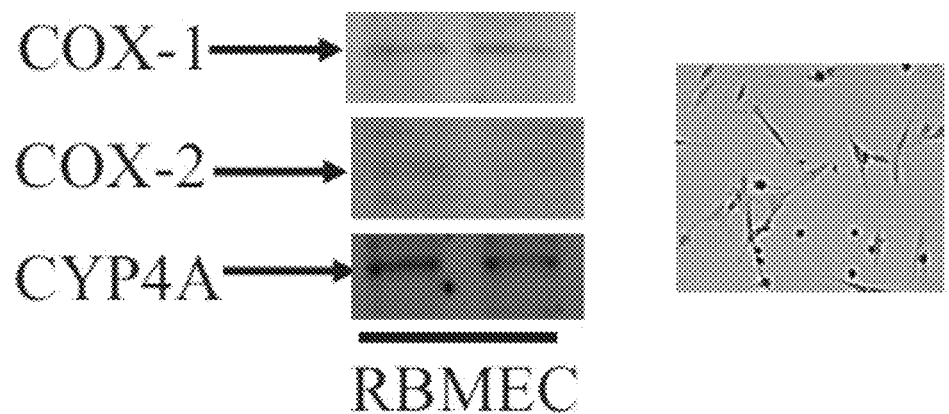
Figure 7C:
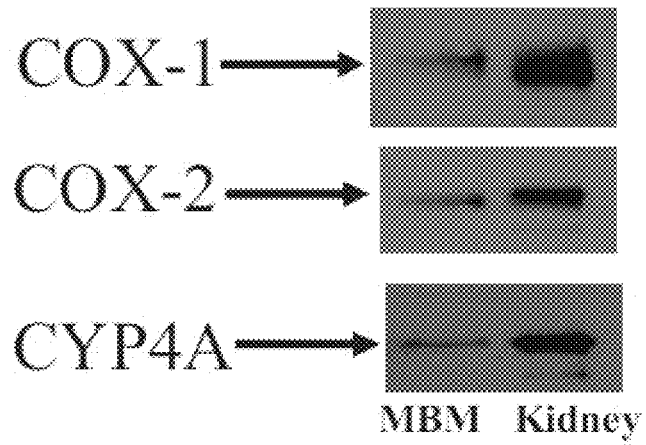

It is possible that increased circulating 20-HETE levels by rofecoxib are a result of a decrease in metabolism by COX-2 because 20-HETE can be metabolized by COX enzymes (Carroll, et al., *J Pharmacol Exp Ther,* 260:104-109 (1992)); Oyekan, *J Pharmacol Exp Ther,* 313:1289-1295 (2005); Schwartzman, et al., *J Biol Chem,* 264:11658-11662, 1989). To investigate whether the cerebrovasculature has the capacity to synthesize and metabolize 20-HETE, the expression COX-1, COX-2, and Cyp4a was determined in a human cerebral microvascular endothelial cell line (HCMECL), primary rat brain microvascular endothelial cells (RBMEC), and mouse brain microvessels (MBM). COX-1 (about 70 kDa), COX-2 (about 72 kDa), and Cyp4a (about 52 kDa) were expressed in HCMECL (FIG. 7A), primary RBMEC (FIG. 7B), and MBM (FIG. 7C). These results provide evidence that the cerebrovasculature is involved in the synthesis and metabolism of 20-HETE across species.

Example 7

Combined Treatment with Rofecoxib and HET0016 Reduces the Adverse Effects of Rofecoxib on Ischemic Stroke Materials and Methods
Assessment of Neurovascular Injury and Functional Outcome After Ischemic Stroke
MC38 tumor mice were divided into three treatment groups and treated for 3 weeks with: rofecoxib (50 mg/l), rofecoxib (50 mg/l) plus HET0016 (5 mg/kg/day, i.p.), or vehicle. Age-matched non-tumor mice were usedas control. At the end of the treatment period, mice were subjected to thromboembolic stroke. Under isoflurane anesthesia, the right common carotid artery, the right external carotid artery (ECA), and the right internal carotid artery were exposed through a middle incision on the ventral side of the neck. A PE 10 catheter containing a fibrin-rich clot was gently inserted from the ECA stump into the distal internal carotid artery just proximal to the origin of the middle cerebral artery (MCA). Each clot (~1 cm), prepared from a donor mouse, was injected with 75 µl of sterile PBS; after 2 min, the catheter was withdrawn as described previously (Hoda, et al., *Exp Transl Stroke Med* 3:16 (2011)). Occlusion was confirmed by a ≥70% drop in cerebral blood flow as compared to the pre-ischemic value. The success rate of thromboembolic MCA occlusion was 95% based on changes in cerebral blood flow. At day 3 after surgery, mice were first evaluated for functional outcome, then sacrificed for evaluation of neurovascular injury including infarct size and bleeding. Extracted brains were analyzed for infarct size in coronal slices of 2 mm thickness, labeled A-G, front to back. Hemorrhagic transformation (HT), secondary bleeding into the brain after ischemic stroke was evaluated by the presence of visible macroscopic bleeding and measured in a binary fashion: yes or no. Number of animals that had HT was reported per group. 2, 3, 5-Triphenyltetrazolium chloride (TTC), a mitochondria stain, was used to outline the infarct area. The captured images were numerically labeled and analyzed using specialized KS300 software. Infarct size was expressed as a percentage of the contralateral hemisphere. Neurologic deficits in mice given different treatments were assessed at 24 h and 72 h after stroke, using a 5-point scale for scoring: 0, no deficit; 1, forelimb flexion deficit on contralateral side; 2, decreased resistance to lateral push and torso turning to the ipsilateral side when held by tail; 3, significant circling to the affected side and reduced capability to bear weight on the affected side; 4, rarely moved spontaneously and preferred to stay at rest.

Figure 8A:
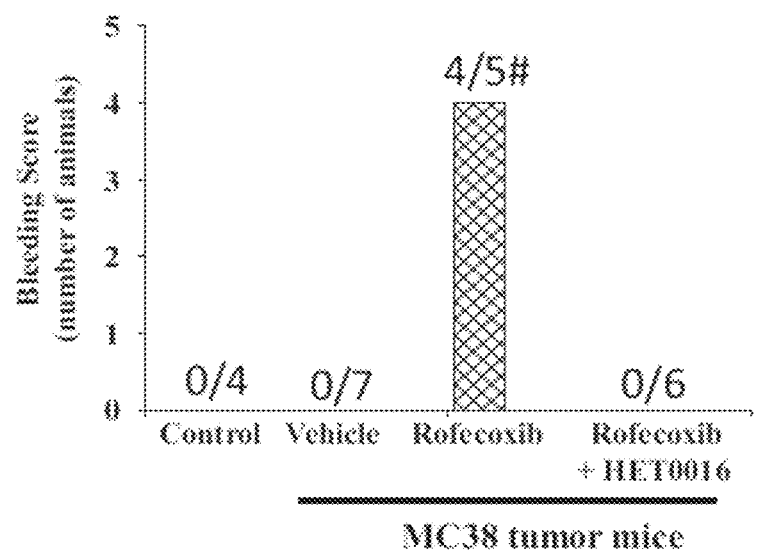
FIG. 8A shows the presence of bleeding was evaluated as a measure of vascular injury in MC38 colon tumor-bearing mice treated with vehicle, rofecoxib (50 mg/l), or rofecoxib+HET0016 (5 mg/kg/day, i.p.), as well as control mice (non-tumor), subjected to ischemic stroke using a modified thromboembolic model. #$P=0.0008$ (Fisher's exact test).
Figure 8B:
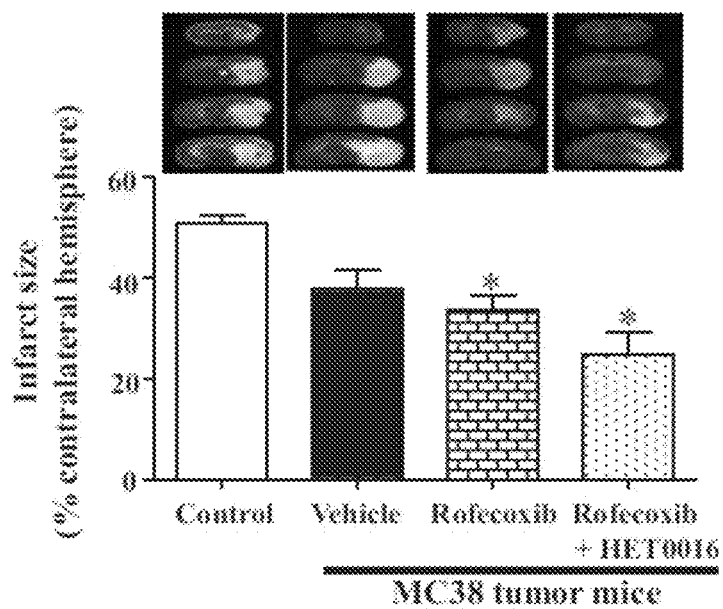
FIG. 8B shows infarct size in vehicle, rofecoxib (50 mg/l), or rofecoxib+HET0016 treated groups. *$P<0.05$ versus vehicle. A representative image from each group is shown above the figure.
Figure 8C:
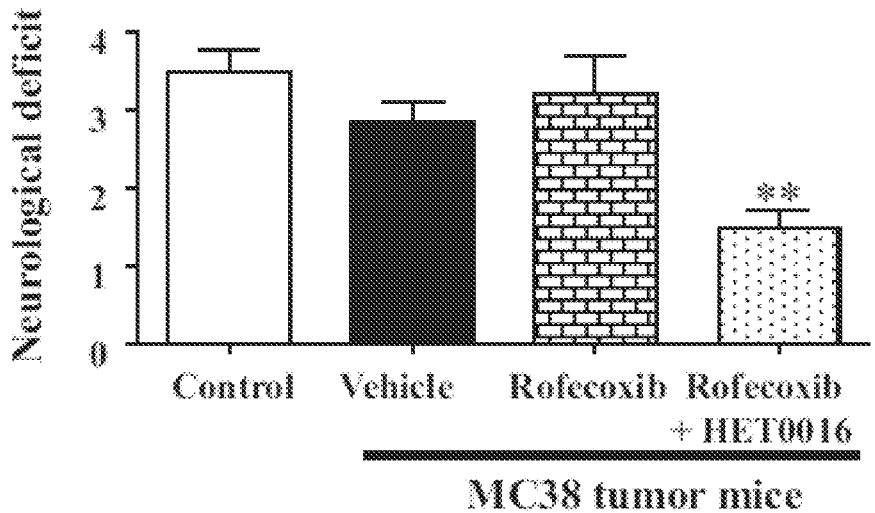
FIG. 8C shows functional outcome in vehicle, rofecoxib (50 mg/l), or rofecoxib+HET0016 treated groups as measured by neurological deficit score. **$P<0.01$ versus other groups. n=4 in control and n=5-7 in other groups.

Results
Since chronic treatment with rofecoxib significantly increased plasma 20-HETE levels (FIG. 6A), the question of whether co-treatment with 20-HETE inhibitor would alter the adverse effects of rofecoxib on ischemic stroke during anti-tumor therapy was investigated. MC38 colon tumor-bearing mice treated with vehicle, rofecoxib, or rofecoxib plus HET0016, as well as control mice (non-tumor), were subjected to ischemic stroke using a modified thromboembolic model that closely mimics ischemia/reperfusion injury in patients with acute ischemic stroke. The data shows that cerebrovascular damage was significantly increased after ischemic stroke in the rofecoxib-treated group (as shown by an 80% occurrence rate of bleeding) as opposed to no visible bleeding in the other groups (FIG. 8A). In addition, mortality was ~30% in the rofecoxib group as compared to 15% in other groups, indicating that rofecoxib had deleterious effects on the brain during anti-tumor therapy. Rofecoxib also reduced the size of infarcts as compared to those in control mice. There was a trend toward further decrease in infarction size with HET0016 treatment (FIG. 8B). Although there appeared to be a decrease in infarct size in the vehicle-treated tumor mice, this did not reach statistical significance (FIG. 8B). Despite reduced infarct size, neurological deficit scores were higher in the rofecoxib group. However, treatment with rofecoxib+HET0016 significantly improved functional outcome (FIG. 8C). Thus, combination treatment with HET0016 and rofecoxib significantly reduced the rofecoxib-induced adverse stroke events during anti-tumor therapy.

Discussion
Although substantial evidence from APC (Adenocacinoma Prevention with Celecoxib), APPROVe (Adenomatous Polyp Prevention on VIOXX), and PreSAP (Prevention of Colorectal Sporadic Adenomatous Polyps clinical trials demonstrates that coxibs reduce the incidence of CRC or even prevent it (Arber, et al., *Am J Gastroenterol*, 106:1135-1146 (2011)); Bertagnolli, et al., *N Engl J Med* 355:873-884 (2006)); Bresalier, et al., *N Engl J Med* 352:1092-1102 (2005)), the increased risk of side effects, including stroke and cardiovascular events, stopped the use of coxibs as cancer preventive agents. The prevailing theory to explain the adverse cardiovascular effects of coxibs is that they reduce the production of $PGI_2$, a potent inhibitor of platelet aggregation, but do not affect the production of thromboxane A2 (TXA2), a potent platelet-aggregating agent (FitzGerald, *N Engl J Med* 351:1709-1711 (2004). Thus, stroke and the cardiovascular complications caused by coxibs might be a consequence of a shifting balance between the levels of $PGI_2$ and TXA2 (Funk, et al., *J Cardiovasc Pharmacol*, 50:470-479 (2007)). Although this theory is attractive, it cannot fully explain why other nonselective COX inhibitors, including diclofenac, ibuprofen, naproxen, and indomethacin, also significantly increase the risk of side effects (Liu, et al., *Proc Natl Acad Sci USA* 107:17017-17022 (2010)). Hence, more complex mechanisms may be responsible for the coxib-induced side effects.

Chronic administration of rofecoxib has been shown to increase 20-HETE levels without affecting other eicosanoid pathways (Liu, et al., *Proc Natl Acad Sci USA* 107:17017-17022 (2010)). 20-HETE has well-characterized detrimental effects on cerebral circulation (Renic, et al., *J Cereb Blood Flow Metab* 29: 629-639 (2009)) and it promotes the growth of tumors in the brain (Guo, et al., *J Pharmacol Exp Ther* 317: 97-108 (2006)), kidney (Alexanian, et al., *Anticancer Res* 29:3819-3824 (2009)), and lung (Yu, et al., *Cancer Chemother Pharmacol* 68: 619-629 (2011)). The data shows that the expression of Cyp4a is absent in normal colon tissue, whereas its expression is up-regulated in colon carcinoma cells (FIG. 1A), and that increasing 20-HETE may play important role in CRC development.

The data show that 20-HETE is produced in MC38 cells (FIG. 1). It is well known that 20-HETE synthesis is primarily catalyzed by the CYP4A gene family (Roman, *Physiol Rev,* 82:131-185 (2002)). In the mouse, four isoforms have been identified: Cyp4a10, Cyp4a12a, Cyp4a12b, and Cyp4a14. Using baculovirus and Sf9 insect cells, Muller and colleagues (Muller, et al., *Biochem J,* 403:109-118 (2007)), in a study of the hydroxylation of AA by mouse Cyp4a isoforms, demonstrated that AA ω-hydroxylation is catalyzed by Cyp4a10, Cyp4a12a, and Cyp4a12b. Cyp4a12a and Cyp4a12b have similar catalytic activity for 20-HETE production, with a Vmax value about 10 min-1 and a Km value about 20-40 µM. Furthermore, the ω-hydroxylase activity of AA for Cyp4a10 is about 25-75 fold lower than that of Cyp4a12 isoforms. Therefore, it is possible that one of the mouse Cyp4a isoforms is responsible for 20-HETE synthesis in MC38 cells.

Figure 3A:
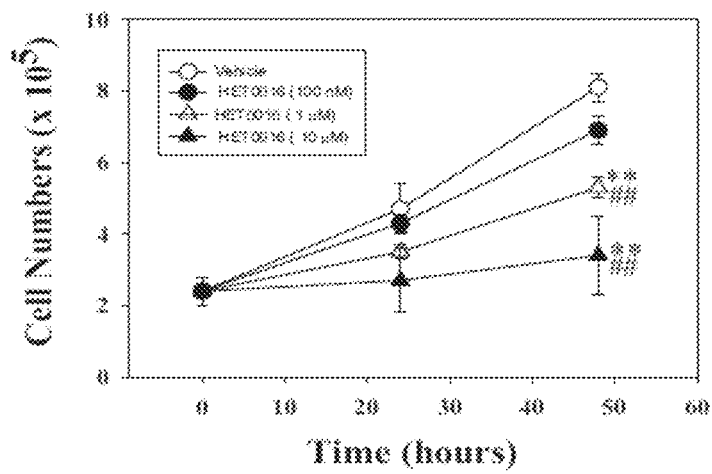
FIGS. 3A-C show the effects of HET0016, rofecoxib, and rofecoxib+HET0016 on MC38 cell proliferation. MC38 cells growing in 6-well plates were treated with (FIG. 3A) HET0016 (100 nM to 10 μM), (FIG. 3B) rofecoxib (100 nM to 10 μM), or (FIG. 3C) HET0016 (1 μM)+rofecoxib (1 μM) for 48 h. Results are expressed as cell number/well and are mean±SE. n=5. *P<0.05, **P<0.01 versus vehicle; #P<0.05, ##P<0.01 versus other groups.
Figure 3B:
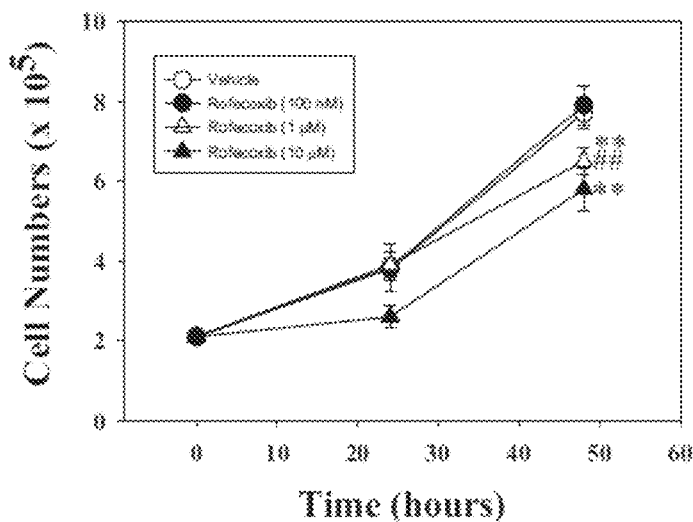
Figure 3C:
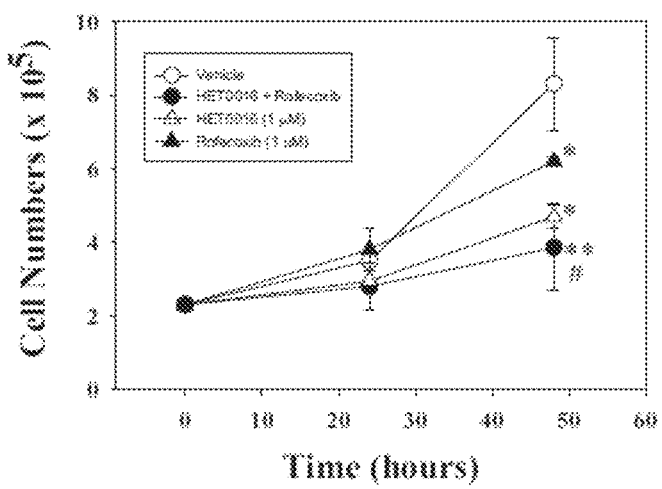

The data presented herein demonstrated that HET0016 dose-dependently inhibited the growth and proliferation of MC38 cells (FIGS. 3A and 4A). It is possible that 20-HETE stimulates MC38 cell proliferation by increasing oxidative stress and promoting angiogenesis, but also induces the phosphorylation of extracellular signal-regulated kinase ½, cyclin D ½, and vascular endothelial growth factor (VEGF) in U251 cell, the mechanism shown by Guo, et al., upon over-expression of CYP4A1. Interestingly, Guo, et al., *J Pharmacol Exp Ther* 327:10-19 (2008) showed that over-expression of CYP4A1, a potent 20-HETE synthase while having negligible ability to form EETs (Guo, et al., *J Pharmacol Exp Ther* 327:10-19 (2008); Nguyen, et al., *Am J Physiol* 276:R1691-R1700 (1999)), induces hyperproliferative phenotype in human glioma cells (U251). They also demonstrated that elevated 20-HETE levels not only increases oxidative stress and promotes angiogenesis, but also induces the phosphorylation of extracellular signal-regulated kinase ½, cyclin D ½, and vascular endothelial growth factor (VEGF) in U251 cells.

The next question addressed was whether the combined therapy with rofecoxib and HET0016 would have an increased inhibitory effect on the proliferation of colon cancer cells in vitro and tumor growth in vivo, in order to determine whether 20-HETE inhibition enhances the anti-tumor effects of COX-2 inhibitor in colon cancer cells. The data shows that although monotherapy with either HET0016 or rofecoxib reduced the proliferation of MC38 cells and tumor growth, greater anti-proliferative and anti-tumor effects were obtained when rofecoxib was administered in combination with HET0016 (FIG. 4 and FIG. 5).

Although the present study provided new information about the additional inhibitory effect of rofecoxib+HET0016 on the growth of colon tumor, the exact mechanisms whereby this combination blocked tumor growth were still not known. Without being bound by any one theory, it is possible that $PGE_2$, the major COX-2-derived PG, was mainly present in the medium of MC38 cells (FIG. 2B), which is consistent with the notions that PGE2 is secreted by cancer cells and that multidrug resistance protein 4 (MRP 4) is involved in this process (Reid, et al., *Proc Natl Acad Sci USA*, 100:9244-9249 (2003)). Thus, the action of $PGE_2$ to promote MC38 tumor growth may have been mediated through its paracrine and autocrine action. It is well known that $PGE_2$ promotes the growth of CRC by stimulating angiogenesis and cell proliferation as well as inhibiting apoptosis (Wang, *Oncogene* 29:781-788 (2010)). Therefore, it is possible that the enhanced inhibitory effect of rofecoxib by HET0016 (FIG. 5B) on tumor growth was because this combination blocked both the paracrine/autocrine action of $PGE_2$ and mitogenic and angiogenic action (Alexanian, et al., *Anticancer Res* 29:3819-3824 (2009); Guo, et al., *J Pharmacol Exp Ther* 327:10-19 (2008); Yu, et al., *Cancer Chemother Pharmacol* 68: 619-629 (2011)) of 20-HETE in colon cancer cells. Moreover, because CRC is a heterogeneous disease, involving multiple dysregulated pathways (Venkatesan, et al., *Life Sci,* 91:789-799 (2012); Wang, *Oncogene* 29:781-788 (2010)), the co-treatment therapy with rofecoxib and HET0016 may increase therapeutic efficacy.

To determine whether 20-HETE inhibition reduces the adverse effects of rofecoxib on stroke during anti-tumor therapy, the following questions were addressed: Does prolonged use of rofecoxib elevate 20-HETE levels? If so, does 20-HETE inhibitor attenuate the adverse effects on stroke during anti-tumor therapy? The data shows that 3 weeks of anti-tumor therapy with rofecoxib significantly increased circulating 20-HETE levels (FIG. 6). This increase was highly selective because rofecoxib treatment did not affect levels of EETs/DHETs, 5-HETE, 8-HETE, 11-HETE, or 15-HETE (FIG. 6).

The exact mechanisms whereby rofecoxib induces 20-HETE are still unknown. Since rofecoxib treatment does not affect the expression of Cyp4a in the liver and kidney of MC38 tumor mice (FIG. 6C), the reason for the induction of circulating 20-HETE levels by rofecoxib (FIG. 6A) may not be a consequence of the increases in endogenous 20-HETE synthesis. It is well established that 20-HETE can be metabolized by COXs into PGs such as 20-OH PGE2 and 20-OH PGF2α (Carroll, et al., *J Pharmacol Exp Ther* 260:104-109 (1992); Liu, et al., *Proc Natl Acad Sci USA* 107:17017-17022 (2010)). Therefore, it is possible that the increase in 20-HETE levels induced by prolonged use of rofecoxib in vivo is caused by inhibition of the metabolizing pathways of 20-HETE by COXs enzymes in brain microvessels. To test this possibility, whether the cerebrovasculature has the capacity to carry out 20-HETE synthesis and metabolism was investigated. The data herein shows that COX-1, COX-2, and CYP4A are expressed in HCMECL, RBMECs, and MBM (FIG. 7), providing evidence that the cerebrovasculature is involved in 20-HETE synthesis and metabolism.

To determine whether chronic treatment with rofecoxib causes the adverse effects associated with stroke, non-tumor mice and MC38 tumor mice treated with vehicle, rofecoxib, or rofecoxib+HET0016 were subjected to embolic stroke using a humanized clot model. HT (Hemorrhagic transformation), which is secondary bleeding into the brain after an ischemic event, is an important complication of ischemic stroke. Studies have shown that disability and death occur more frequently in ischemic stroke patients who develop HT (Kunte, et al. m Ann Neurol., 72:799-806 (2012)). HT was significantly increased in rofecoxib-treated mice. 4 out of the 5 animals in that group developed HT, whereas there was no visible bleeding in the other groups (FIG. 8). Thus, chronic administration of rofecoxib was associated with increased complications of ischemic stroke. These results are in agreement with clinical data showing long-term use of rofecoxib is associated with a risk of stroke (Bresalier, et al., *N Engl J Med* 352:1092-1102 (2005); 36). It is well known that 20-HETE is a potent vasoconstrictor of cerebral arteries (Gebremedhin, et al., *J Physiol* 507 (Pt 3):771-781 (1998)); it also increases platelet aggregation and shortens bleeding time (Liu, et al., *Proc Natl Acad Sci USA* 107:17017-17022 (2010)); it contributes to the development of cerebral vasospasm (Roman, et al., *Neurol Res* 28: 738-749 (2006)); it also contributes to neuronal cell death after ischemia-reperfusion injury (Renic, et al., *J Cereb Blood Flow Metab* 29:629-639 (2009)); and it is involved in neuronal excitotoxicity in vivo (Yang, et al., *J Neurochem* 121: 168-179 (2012)). It is possible that elevated levels of 20-HETE induced by rofecoxib during anti-tumor therapy (FIG. 6) trigger the detrimental action of 20-HETE in cerebral circulation, thereby causing the adverse effects associated with ischemic stroke. Notably, combined treatment with rofecoxib+HET0016 attenuated the adverse effects associated with ischemic stroke induced by rofecoxib (FIG. 8). These results demonstrate that this combination therapy can enhance anti-tumor effects, but reduce deleterious cerebrovascular events.

Previous studies documented that 20-HETE analogues, including WIT0013 and 5, 14, 20-HEDGE, and 20-HETE antagonist (WIT002) are important tools to study the function of 20-HETE pathway in vivo. For example, Regner et al. (Regner, et al., *Kidney Int* 75:511-517 (2009)) found that 5, 14, 20-HEDGE protects kidney from ischemia-reperfusion injury. Another report (Yu, et al., *Eur J Pharmacol* 486:297-306 (2004)) demonstrated that WIT0013 increases cerebral vascular tone, whereas WIT002 attenuates 20-HETE-induced vasoconstriction response in vascular smooth muscle cells. Thus, one embodiment provides compositions containing a 20-HETE analogue that can be used to inhibit or prevent coxib-induced cerebrovascular damage.

Perspectives and Significance: 20-HETE is produced in colon cancer cells, where it promotes the proliferation of cancer cells and tumor growth. In vitro and in vivo, combined treatment with rofecoxib+HET0016 displayed greater anti-proliferative and anti-tumor effects than did rofecoxib alone. The LC/MS/MS analysis supported the notion that prolonged use of rofecoxib increases circulating 20-HETE levels, which could trigger cerebrovascular events, during anti-tumor therapy. It appears that combination with rofecoxib and HET0016 significantly reduces rofecoxib-induced cerebrovascular damage and stroke outcomes. Therefore, this study provides a novel intervention strategy that concurrent inhibition of 20-HETE and COX-2 can not only enhance anti-tumor efficacy of coxibs, but also prevent coxib-induced adverse stroke events.

Example 8

Rofecoxib Inhibits 20-OH $PGE_2$ Synthesis

Materials and Methods

Purified COX-2 was incubated with 5 µM 20-HETE in buffer containing 1 µM hematin and 2 mM L-epinephrine at 37° C. for 3 min. After purification, a major metabolite was isolated subjected to LC/MS/MS analysis. This metabolite exhibits a mass spectrum identical to 20-OH $PGE_2$.

Results

Since rofecoxib administration does not affect Cyp4a expression in different tissues, it was believed that increased circulating 20-HETE levels by rofecoxib are a result of a decrease in 20-HETE metabolism by COX-2. Therefore, whether COX-2 could metabolize 20-HETE was examined. Notably, incubation of purified COX-2 with 20-HETE and co-factors generated a major PG metabolite (FIG. 9A), which exhibits a mass spectrum that is identical to that of 20-OH $PGE_2$. Strikingly, rofecoxib at 1 µM inhibited 20-OH $PGE_2$ by 70% (FIG. 9B), providing direct evidence that COX-2 metabolizes 20-HETE into 20-OH $PGE_2$ and that rofecoxib impairs 20-HETE metabolism by COX-2.

Example 9

20-OH PGE2 Supplementation Reduces Cerebral Injury and Improves Functional Recovery After Stroke Materials and Methods B6 mice were divided into two groups: one supplemented with 20-OH $PGE_2$ (250 ng/h in an osmotic pump) and one given vehicle. After one week of treatment, the mice were subjected to ischemic stroke.

Results

Although 20-OH $PGE_2$ elicits beneficial protective effects in brain endothelial cells under OGD/Rep, the precise role of 20-OH $PGE_2$ in ischemic stroke is still to be defined. To determine the effects of 20-OH $PGE_2$ supplementation on stroke damage, B6 mice were treated with 20-OH $PGE_2$ (Cayman) (administered via an osmotic pump (Alzet) at a dose of 250 ng/h) or vehicle for 7 days. The effects of 20-OH $PGE_2$ on infarct size and neurological deficit after ischemic stroke were examined. Strikingly, 20-OH $PGE_2$ supplementation reduced both infarct size (FIG. 10A) and neurological deficits (FIG. 10B), demonstrating that 20-OH $PGE_2$ supplementation elicits cerebroprotection by reducing cerebral injury and improving functional recovery after stroke.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

I claim:

1. A pharmaceutical composition comprising an effective amount of a COX-2 inhibitor to inhibit cancer cell growth in a subject in need thereof in combination with a 20-Hydroxyeicosatetraenoic acid (20-HETE) antagonist in an effective amount to reduce or inhibit side effects of the COX-2 inhibitor in the subject, wherein the COX-2 inhibitor is selected from the group consisting celecoxib, rofecoxib, etoricoxib, valdecoxib, 4-[5-(4-methylphenyl)-3-(methylselenocyano)-1H-pyrazol-1-yl]benzene-sulfonamide, 4-[5-(4-(methylselenomethylene)phenyl)-3-(trifluoromethyl)-1H-pyrazol-1-yl]benzene-sulfonamide and 2,5-dimethyl-celecoxib and wherein the 20-HETE antagonist is selected from the group consisting of 20-hydroxyeicosa-6(Z),15(Z)-dienoic acid (WIT002), N-Hydroxy-N'-(4-butyl-2-methylphenyl)formamidine (HET0016), 17-octadecynoic acid (17-ODYA), N-methylsulfonyl-12,12-dibromododec-11-enamide (DDMS), dibromododec-11-enoic acid (DDBB), N-(3-Chloro-4-morpholin-4-yl)Phenyl-N'-hydroxyimido formamide (TS011), 20-hydroxyeicosa-6(Z),15 (Z)-dienoic acid (6-,15-,20-HEDE) and (N-[20-hydroxyeicosa-5 (Z), and 14 (Z)-dienoic acid (5, 14, 20-HEDGE).

2. The pharmaceutical composition of claim 1, further comprising an excipient.

3. The pharmaceutical composition of claim 1 or 2, wherein the COX-2 inhibitor is rofecoxib and the 20-HETE blocker is HET0016.

4. The pharmaceutical composition of claim 1, wherein the side effects are selected from the group consisting of myocardial infarction, arterial and venous thrombic events, ischemic stroke, and arrhythmia.

5. The pharmaceutical composition of claim 1, wherein the pharmaceutical composition is formulated for enteral administration.

6. The pharmaceutical composition of claim 1, wherein the pharmaceutical composition is formulated for parenteral administration.

7. A method for inhibiting cancer cell growth in a subject, comprising:
administering to the subject the pharmaceutical composition of claim 1.

8. A method for reducing the reoccurrence of cancer in a subject, comprising:
administering the pharmaceutical composition of claim 1 to the subject.

9. The method of claim 8, wherein the cancer is colorectal cancer.

10. The method of claim 9, wherein a colorectal adenoma or poly is removed from the subject prior to administration of the pharmaceutical composition.

11. A method for reducing the reoccurrence of colorectal adenoma in a subject in need thereof, comprising:
administering the pharmaceutical composition of claim 1 to the subject.

* * * * *